(12) United States Patent
Arora et al.

(10) Patent No.: US 7,691,889 B2
(45) Date of Patent: Apr. 6, 2010

(54) ANTIMYCOBACTERIAL COMPOUNDS

(75) Inventors: Sudershan Kumar Arora, Maharashtra (IN); Vijaykumar Jagdishwar Patil, Maharashtra (IN); Prathap Sreedharan Nair, Maharashtra (IN); Prasad Purushottam Dixit, Maharashtra (IN); Shankar Ajay, Maharashtra (IN); Rakesh Kumar Sinha, Maharashtra (IN)

(73) Assignee: Lupin Limited, Kalina, Santacruz (East), Mumbai, Maharashtra (IN)

( * ) Notice: Subject to any disclaimer, the term of this patent is extended or adjusted under 35 U.S.C. 154(b) by 1338 days.

(21) Appl. No.: 11/082,947

(22) Filed: Mar. 18, 2005

(65) Prior Publication Data

US 2005/0192275 A1    Sep. 1, 2005

(30) Foreign Application Priority Data

Sep. 20, 2002    (WO) .................. PCT/IN02/00190

(51) Int. Cl.
*A61K 31/422*    (2006.01)
*A61K 31/5377*   (2006.01)
*A61K 31/541*    (2006.01)
*A61K 31/454*    (2006.01)
*A61K 31/496*    (2006.01)
*C07D 263/20*    (2006.01)
*C07D 413/02*    (2006.01)
*C07D 417/02*    (2006.01)

(52) U.S. Cl. .................. 514/376; 514/236.8; 514/227.8; 514/326; 514/254.04; 544/137; 544/60; 544/367; 546/209; 548/229

(58) Field of Classification Search ................ 546/209; 544/137, 60, 367; 548/229; 514/236.8, 227.8, 514/326, 254.02, 376
See application file for complete search history.

(56) References Cited

U.S. PATENT DOCUMENTS

| 4,942,183 A | 7/1990 | Gregory et al. |
| 4,948,801 A | 8/1990 | Carlson et al. |
| 5,529,998 A | 6/1996 | Habich et al. |
| 5,565,571 A | 10/1996 | Barbachyn et al. |
| 5,652,238 A | 7/1997 | Brickner et al. |
| 5,654,428 A | 8/1997 | Barbachyn et al. |
| 5,684,023 A | 11/1997 | Riedl et al. |
| 5,688,792 A | 11/1997 | Barbachyn et al. |
| 5,719,154 A | 2/1998 | Tucker et al. |
| 5,736,545 A | 4/1998 | Gadwood et al. |
| 5,756,732 A | 5/1998 | Barbachyn et al. |
| 5,792,765 A | 8/1998 | Riedl et al. |
| 5,801,246 A | 9/1998 | Barbachyn et al. |
| 5,861,413 A | 1/1999 | Habich et al. |
| 5,880,118 A | 3/1999 | Barbachyn et al. |
| 5,929,248 A | 7/1999 | Barbachyn et al. |
| 6,069,160 A | 5/2000 | Stolle et al. |
| 6,124,334 A | 9/2000 | Hutchinson |
| 6,227,868 B1 | 5/2001 | Wlodarski |
| 6,410,728 B1 | 6/2002 | Sciotti et al. |

FOREIGN PATENT DOCUMENTS

| WO | WO 93/23384 | 11/1993 |
| WO | WO 95/07271 | 3/1995 |
| WO | WO 97/10223 | 3/1997 |
| WO | WO 98/01446 | 1/1998 |
| WO | WO 98/01447 | 1/1998 |
| WO | WO 99/02525 | 1/1999 |
| WO | PCT/US99/01318 | 7/1999 |
| WO | WO 99/37630 | 7/1999 |
| WO | WO 99/37641 | 7/1999 |
| WO | WO 01/09107 | 2/2001 |
| WO | WO 01/42242 | 6/2001 |
| WO | WO 02/06278 | 1/2002 |
| WO | WO 02/20515 | 3/2002 |
| WO | WO 2004/026848 | 4/2004 |

OTHER PUBLICATIONS

Hass, C, PCT Written Opinion of PCT/IN 02/00190, Jun. 1, 2004.
S. Majumdar, Response to Written Opinion of PCT/IN02/00190, May 4, 2004.
Examiner, PCT Written Opinion of PCT/IN02/00190, Mar. 11, 2004.
S. Majumdar, Response to Written Opinion of PCT/IN02/00190, Aug. 30, 2004.
Halbartschlager, M, Int'l Prel Exam Report of PCT/IN02/00190, Sep. 21, 2004.
Tanja R}Hrmung, Int'l Search Report of PCT/IN02/00190, Jul. 24, 2003.

*Primary Examiner*—Rebecca L Anderson
*Assistant Examiner*—Jason M Nolan
(74) *Attorney, Agent, or Firm*—Lau & Associates, LLC.

(57) ABSTRACT

Novel compounds belonging to the class of oxazolidinones possessing potent antimycobacterial properties especially useful in the treatment of acid fast organisms such as *Mycobacterium tuberculosis*, *Mycobacterium avium*-intracellular complex, *M. fortuitum* and *M. kansai*. The compound and its pharmaceutically acceptable salts act as antibacterial agents. Also mentioned is a method for inhibiting growth of mycobacterial cells as well as a method of treating mycobacterial conditions such as *Mycobacterium tuberculosis*, drug resistant *Mycobacterium tuberculosis*, *Mycobacterium avium*-intracellular complex, *M. fortuitum* and *M. kansai*., including administering an antimycobacterially effective amount of the compound and/or pharmaceutically acceptable salts. There is also mentioned a process for the manufacture of the compound or its pharmaceutically acceptable salts.

16 Claims, No Drawings

ANTIMYCOBACTERIAL COMPOUNDS

FIELD OF THE INVENTION

The present invention relates to novel compounds belonging to the class of oxazolidinones useful in the treatment of acid fast organisms such as *Mycobacterium tuberculosis*, *Mycobacterium avium* and *Mycobacterium* spp. The present invention further relates to methods for preparation of the novel compounds and to pharmaceutical compositions containing the novel compounds useful in the treatment of tuberculosis.

BACKGROUND OF THE INVENTION

Tuberculosis (TB), an infectious disease caused by the bacterium *Mycobacterium tuberculosis* is transmitted mainly through air, affecting most often the lungs. When persons with pulmonary TB cough they produce tiny droplet nuclei containing *M. tuberculosis*, which remain suspended in air for a prolonged period of time. A person who breathes the air containing the aforesaid droplet nuclei containing *M. tuberculosis* can become infected with TB.

TB, one of the three major infectious diseases in the priority list of the World Health Organization's (WHO) agenda kills about two million people around the world every year. About six million new cases are reported every year and nearly 20% of adult deaths and 6% of infant deaths are attributable to the disease (C. Dye et. al., J. Am. Med. Ass., 1999, 282, 677-686). About a billion people are expected to be affected by TB by the year 2020, with 35 million likely to succumb to the disease (WHO Fact Sheet No. 104, Global Alliance for TB Drug Development—Executive Summary of the Scientific Blueprint for TB Development www.who.int/inf-fs/en/fact104).

With the emergence of the AIDS epidemic and the increase in cases of HIV coupled with TB as well as the continued resistance of *M. tuberculosis* to isoniazid and rifampicin, the two most powerful anti-tubercular drugs available today there is an urgent need for new anti-tubercular drugs to combat the killer disease (S. H. E. Kaufmann et. al., *Trends Microbiol.*, 1993, 1, 2-5 B. R. Bloom et. al., *N. Engl. J. Med.*, 1998, 338, 677-678).

Although, many new compounds are becoming available for fighting a number of infectious diseases, the number of such compounds having antimycobacterial activity are few. This could partly be due to the complexity of research involved and partly due to business considerations (B. N. Roy et. al., *J. Ind. Chem. Soc.*, April 2002, 79, 320-335 and references cited therein).

However, renewed thrust in research in the last decade has resulted in development of new antimycobacterial compounds,
a) differing widely in structures,
b) having different mode/mechanism of action,
c) possessing favourable pharmacokinetic properties,
d) which are safe and have low incidence of side-effects, and
e) which provide a cost-effective dosage regimen.

Among the aforesaid new compounds, the oxazolidinones first developed during the mid-1980s (W. A. Gregory et. al., *J. Med. Chem.*, 1989, 32, 1673-1681 and 1990, 33, 2569-2578; C-H Park et. al., *J. Med. Chem.*, 1992, 35, 1156-1165) are a unique class in themselves. The in vivo results for some of the oxazolidinones show that they are active against various Gram-positive bacteria such as staphylococci, pneumococci and enterococci, including resistant strains such as methicillin-resistant *Staphylococcus aureus* [MRSA], methicillin-resistant *Streptococcus epidermidis* [MRSE], penicillin-resistant *Streptococcus pneumoniae* [PRSP], vancomycin-resistant enterococci [VRE], etc. (B. Riedl et. al., *Exp. Opin. Ther. Patents.*, Ashley Publications Ltd., 1999, 9 (5), 625-633 and the references contained therein).

The oxazolidinones inhibit bacterial protein synthesis at a very early step in the initiation of complex formation involved in the process of translating mRNA into protein. The oxazolidinones, in general, are not cross-resistant with any known antibiotic because of this unique mechanism (D. C. Eustice et. al., *Antimicrob. Agents Chemother.*, 1988, 32, 1218 and *Biochem. Biophys. Res. Commun.*, 1988, 150, 965).

A feature of the oxazolidinone molecule is that only those compounds, which are enantiomers with a (5S)-acetamidomethyl configuration in the left side of the molecule are known to exhibit antibacterial activity (W. A. Gregory et. al., *J. Med. Chem.*, 1989, 32, 1673-1681). Another feature is that most of such antibacterial compounds invariably carry a (substituted) phenyl ring attached to the nitrogen atom of the oxazolidinone ring in the right side of the molecule (B. Riedl et. al., *Exp. Opin. Ther. Patents.*, Ashley Publications Ltd., 1999, 9 (5), 625-633 and the references contained therein).

The most promising compound among the N-phenyl oxazolidinones, which has been approved for human use is (S)-N-[[3-[3-fluoro-4-(4-morpholinyl)phenyl]-2-oxo-5-oxazolidin-yl]methyl]-acetamide), commonly known as linezolid (M. Barbachyn et. al., WO 995/07271). Linezolid possesses good in vitro and in vivo potency against most of the Gram-positive bacteria, including resistant strains (*Drugs of the Future*, 1996, 21(11), 1116-1123).

The left hand side i.e. position 5- and the right hand side i.e. position 3-respectively of the oxazolidinone ring nucleus allows for many variations and has resulted in the discovery of a large number of compounds having antimicrobial and antibacterial properties. Such representative compounds, albeit not meant to be limiting are disclosed in the following prior art references. These are i) U.S. Pat. No. 4,942,183 (Gregory et. al.) and U.S. Pat. No. 4,948,801 (Carlson et. al.) collectively disclose certain 3-substituted phenyl-5-aminomethyl oxazolidinones, possessing useful antibacterial activity.

ii) U.S. Pat. No. 5,529,998 (Habich et. al.) discloses certain 3-benzoxazoyl- and benzothiazolyl-5-acetyl amino methyl oxazolidinones, useful as antibacterial medicaments.

iii) U.S. Pat. Nos. 5,565,571, 5,654,428, 5,756,732, 5,801, 246 and 5,929,248 (Barbachyn et. al.) collectively disclose several substituted aryl and heteroaryl phenyloxazolidinones carrying an acetyl aminomethyl function at the 5-position, specifically oxazolidinones having an aryl or heteroaryl group at the para position of the 3-phenyl ring and additional substituents at the meta positions of the 3-phenyl ring, which are useful as antibacterials.

iv) U.S. Pat. No. 5,652,238 (Brickner et. al.) discloses certain 5-acetyl aminomethyl-3-phenyloxazolidinones, substituted at the para position of the 3-phenyl ring with a hydroxyl acetyl piperazine moiety, active against various Gram-positive bacteria such as *staphylococci*, *pneumococci* and *enterococci*, as well as anerobic organisms such as *bacteroides* and *clostridia* species as well as acid-fast organisms such as *Mycobacterium tuberculosis*.

v) U.S. Pat. No. 5,684,023 (Riedl et. al.) discloses certain 3-benzofuranyl- and benzothienyl oxazolidinones, carrying an azido, hydroxy or acetyl aminomethyl group at the 5-position, useful as antibacterial medicaments.

vi) U.S. Pat. No. 5,688,792 (Barbachyn et. al.) discloses certain 5-acetyl aminomethyl-3-phenyloxazolidinones, substituted at the para position of the 3-phenyl ring with a (substituted)-morpholine. Such compounds are useful for treatment of microbial infections caused by staphylococci, streptococci, enterococci, *Bacteroides* spp., *Clostridia* spp., *Mycobacterium tuberculosis, Mycobacterium avium* or *Mycobacterium* spp.

vii) U.S. Pat. No. 5,719,154 (Tucker et. al.) discloses certain 5-acetyl aminomethyl-3-phenyloxazolidinones, substituted at the para position of the 3-phenyl ring with a substituted piperazine moiety, the said substitution being a pyrimidinyl or pyradazinyl group. Such compounds are useful as antimicrobial agents.

viii) U.S. Pat. No. 5,736,545 (Gadwood et. al.) discloses certain 5-acetyl aminomethyl-3-phenyloxazolidinones, substituted at the para position of the 3-phenyl ring with a substituted piperazine moiety, the substitution being a five membered heterocycle ring, in particular an azolyl ring. Such compounds are useful in the treatment of microbial infections.

ix) U.S. Pat. No. 5,792,765 (Riedl. et. al.) discloses certain substituted 5-acetyl aminomethyl-3-substituted phenyloxazolidinones, the substitution being a heterocyclic moiety, useful as antibacterial medicaments.

x) U.S. Pat. No. 5,861,413 (Habich et. al.) discloses certain 2-oxo and 2-thio-1,2-dihydroxyqoinolinyl-1-oxazolidinones, useful as antibacterial medicaments.

xi) U.S. Pat. No. 5,880,118 (Barbachyn et. al.) discloses certain substituted 5-acetyl aminomethyl-3-phenyloxazolidinones, substituted at the para position of the 3-phenyl ring with a substituted thiomorholine moiety i.e. oxazine and thiazine derivatives, useful for treatment of microbial infections caused by staphylococci, streptococci, enterococci, *Bacteroides* spp., *Clostridia* spp., *Mycobacterium tuberculosis, Mycobacterium avium* or *Mycobacterium* spp.

xii) U.S. Pat. No. 5,910,504 and U.S. Pat. No. 6,124,334 (Hutchinson et. al.) collectively disclose certain substituted 5-acetyl aminomethyl-3-phenyloxazolidinones substituted at the para position of the 3-phenyl ring with a heteroaromatic moiety, which is five membered having one to four nitrogen atoms or alternatively, a benzoannulated five-membered heteroaromatic ring having one to four nitrogen atoms, useful as antibacterials.

xiii) U.S. Pat. No. 6,069,160 (Stolle et. al.) discloses certain substituted 5-acetyl aminomethyl-3-benzocyclopentaneoxazolidinones, containing an heteroatom, useful as antibacterial medicaments.

xiv) U.S. Pat. No. 6,227,868 B1 and U.S. Pat. No. 6,410,728 (Sciotti et. al.) collectively disclose certain 5-acetyl aminomethyl-3-phenyloxazolidinones carrying an acetylenic moiety on the 3-phenyl ring, useful for treating bacterial infections, psoriasis, arthritis and toxicity due to chemotherapy.

xv) WO 93/23384 (Hutchinson et. al.) discloses certain substituted 5-acetyl aminomethyl-3-phenyloxazolidinones, substituted at the para position of the 3-phenyl ring with a substituted piperazine moiety, useful for treatment of microbial infections caused by staphylococci, streptococci, as well as anaerobic organisms such as *bacteroides* and *clostridia* species and acid-fast organisms such as *Mycobacterium tuberculosis* and *Mycobacterium avium*.

xvi) WO 97/10223 (Gadwood et. al.) discloses certain substituted 5-acetyl aminomethyl-3-aminoaryl oxazolidinone N-oxide compounds, which are exceedingly water soluble and useful in preparation of pharmaceutical compositions for combating a number of human and veterinary pathogens, staphylococci, streptococci, as well as anaerobic organisms such as *bacteroides* and *clostridia* species and acid-fast organisms such as *Mycobacterium tuberculosis* and *Mycobacterium avium, Mycobacterium* spp. and *Mycoplasma* spp.

xvii) WO 98/01446 and WO 98/01447 (Betts et. al.) collectively disclose certain substituted 5-acetyl aminomethyl3-phenyloxazolidinones, substituted at the para position of the 3-phenyl ring with a substituted piperazine moiety, the substitution being a six-membered heteroaryl ring containing two or three ring nitrogen atoms as the only ring heteroatoms, useful as antibacterial agents.

xviii) WO 99/02525 (Thomasco et. al.) discloses certain substituted 5-acetyl aminomethyl-3-phenyloxazolidinones, substituted by a thiadiazolyl or oxadiazolyl moiety, useful as antimicrobial agents, effective against a number of human and veterinary pathogens, including Gram-positive and Gram-negative aerobic bacteria.

xix) WO 99/37630 (Gordeev et. al.) discloses oxazolidinone combinatorial libraries, compositions containing the same and methods of preparation thereof involving solid phase synthesis, which provides the said compounds for high-throughput screening.

xx) WO99/37641 (Bartel. et. al.) discloses certain substituted 5-acetyl aminomethyl-3-bicyclene-substituted oxazolidinones, useful as antibacterial medicaments.

xxi) WO 01/09107 (Gordeev et. al.) discloses certain 3-heteroaryl-5-acetyl aminomethyl oxazolidinones, substituted by a thioacyl, aminocarbonyl, alkoxycarbonyl, aminothiocarbonyl, alkoxythiocarbonyl and alkylthiocarbonyl group, useful in treating or preventing an infectious disorder in humans or animals.

xxii) WO 01/42242 (Paget et. al.) discloses certain substituted 5-acetyl aminomethyl 3-substituted phenyloxazolidinones, the substitution being a bicyclic heterocyclic system, useful as antibacterial agents.

xxiii) WO 02/06278 (Mehta et. al) discloses certain substituted 3-phenyl oxazolidinones and to process for synthesis of the same, the said compounds useful as antibacterial agents, effective against a large number of human and veterinary pathogens, including Gram-positive bacteria and acid fast organisms such as *Mycobacterium tuberculosis*.

xxiv) WO 02/20515 (Madar et. al.) discloses heterocyclic phenyloxazolidinones, useful for treating bacterial infections.

However, only a few of the disclosures described hereinbefore provide compounds that can be used as antimycobacterials, while most of the others are silent about the antimycobacterial activity of the disclosed compounds.

A need, therefore, exists for new compounds possessing potent antimycobacterial properties for treatment of TB, which as mentioned hereinearlier is assuming alarming proportions.

OBJECTS OF THE INVENTION

It is thus the basic object of the present invention to synthesize, identify and provide new compounds belonging to the class of oxazolidinones, possessing potent antimycobacterial properties especially for treatment of acid fast organisms such as *Mycobacterium tuberculosis, Mycobacterium avium*-intracellular complex, *M. fortuitum* and *M. kansai*.

Another object is directed to providing antimycobacterial pharmaceutical composition effective in inhibiting/treating the generation of mycobacterial conditions/cells including *Mycotacterium tuberculosis*, drug resistant *Mycobacterium tuberculosis, Mycobacterium avium*-intracellular complex, *M. fortuitum* and *M. kansai*.

SUMMARY OF THE INVENTION

Thus according to the basic aspect of the present invention there is provided compound of formula (I) and its pharmaceutically acceptable salts thereof

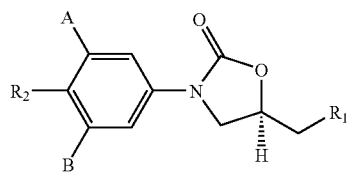

(I)

wherein,

A, B=H, and/or F $R_1$ is a group of formula

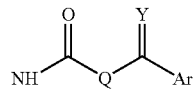

wherein,

Q is $CH_2$—$CH_2$, CH=CH, or C≡C

Y is O, S or $NR_3$ wherein, $R_3$ is $C_1$-$C_4$ alkyl (straight, branched, unsaturated), cycloalkyl, COOH, $COOR_4$, CHO, $COCR_4$, CN, aryl, heteroaryl wherein, $R_4$ is an alkane of 1-4 carbon atoms, an alkene of 3-6 carbon atoms, an alkyne of 3-6 carbon atoms, and Ar is an aromatic carbocycle represented by

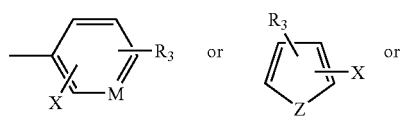

wherein,

X is $OR_4$, $NR_4R_5$, $NO_2$, $SR_4$, $SOOR_4$, $SOONR_4R_5$, Br, Cl, F, or I,

M is —CH or N, and

Z is —CH, —NH, O or S and wherein, $R_3$ and $R_4$ are as described hereinbefore, and $R_5$ is H, or same as $R_4$, and $R_2$ is selected from the groups shown below, and the corresponding N-oxides thereof

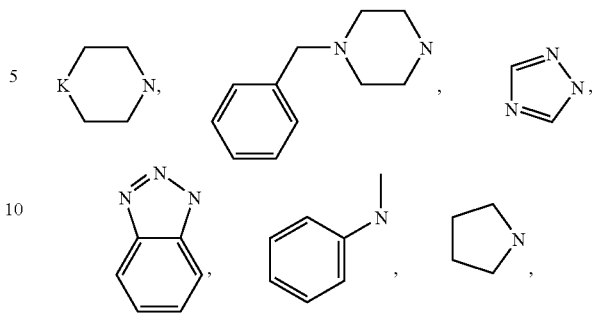

Heteroaryl or Heterocycloalkyl wherein K is O, S, SO, $SO_2$, or $CH_2$

According to another aspect of the invention there is provided a pharmaceutical composition comprising:

i) at least one of an antimycobacterially effective amounts of compound of formula I and pharmaceutically acceptable salts there of; and ii) a pharmaceutically acceptable carrier.

According to yet another aspect of the present invention there is provided a method of inhibiting growth of mycobacterial cells such as *Mycobacterium tuberculosis*, drug resistant *Mycobacterium tuberculosis, Mycobacterium avium*-intracellular complex, *M. fortuitum* and *M. kansai*, comprising administering an antimycobacterially effective amount of the compound of formula I and/or pharmaceutically acceptable salts thereof.

According to yet another aspect of the present invention there is provided a method of treating mycobacterial conditions such as *Mycobacterium tuberculosis*, drug resistant *Mycobacterium tuberculosis, Mycobacterium avium*-intracellular complex, *M. fortuitum* and *M. kansai*, comprising administering an antimycobacterially effective amount of the compound of formula I and/or pharmaceutically acceptable salts thereof.

According to another aspect, there is provided a process for the manufacture of the compound of formula I or its pharmaceutically acceptable salts comprising:

coupling the amino fragments of compound of formula II with the carboxylic acid fragment of formula III.

The above disclosed compound of formula I its pharmaceutically acceptable salts thereof are found to have antimycobacterial properties and the same in admixture with pharmaceutically active additives, an be administrated orally or paranterally for treatement of mycobacterial conditions especially TB.

DETAILED DESCRIPTION OF THE INVENTION

In the pharmaceutically active compound of formula (I) of this invention,

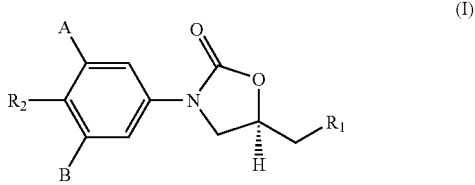

(I)

the definition of the symbols and groups A, B, R₁ and R₂ are as follows:

A is either hydrogen or fluorine,

B is either hydrogen or fluorine,

A and B together is hydrogen and fluorine,

When A is hydrogen, B is fluorine and vice-versa.

R₁ represents a group of formula,

Q is either an alkyl group of two carbon atoms ($CH_2$—$CH_2$), an alkene group of two to carbon atoms (CH=CH), or an alkyne group of two carbon atoms (C≡C)

Y can either be oxygen, sulfur or an amino function of formula $NR_3$, wherein $R_3$ is an alkyl group of 1-4 carbon atoms, both saturated and unsaturated, which can be straight or branched. Suitable alkyl groups are methyl, ethyl, n-propyl, n-butyl, iso-propyl, iso-butyl, tert-butyl, ethylene, propylene, 1, butene, both the geometric isomers of 2-butene i.e. (cis)-2-butene and (trans)-2-butene, and iso-butylene, or $R_3$ is a cycloalkyl group of 3-7 carbon atoms such as cyclopropyl, cyclobutyl, cyclopentyl, cyclohexyl and cycloheptyl, or $R_3$ is a carboxylic acid group (—COOH) or a carboxylic acid ester of formula —$COOR_4$, wherein $R_4$ is H, an alkyl group of 14 carbon atoms, an alkene of 3-6 carbon atoms, an alkyne of 3-6 carbon atoms.

$R_3$ is further an aldehyde (—CHO), an acetyl group (—$COCR_4$), wherein $R_4$ is as mentioned hereinbefore or $R_3$ is a nitrile (CN), aryl or heteroaryl, wherein Aryl is phenyl substituted with (O) or (1) of —F, —Cl, —$OCH_3$, —OH, —$NH_2$, —$C_1$-$C_4$ alkyl, —O—C(O)—$OCH_3$, —$NO_2$ or —CN, and Heteroaryl The group Ar is a substituted phenyl ring or a substituted pyridine ring of formula or Ar is a five membered ring of formula or Ar is a fused bicyclic phenyl or pyridine ring of formula wherein, M is either CH or N; Z is —CH, —NH, O or S and $R_3$ is as defined hereinbefore, X is a group selected from $OR_4$, $NR_4R_5$, $NO_2$, $SR_4$, $SOOR_4$, $SOONR_4R_5$, F, Cl, Br or I, wherein $R_4$ is as defined hereinbefore, and $R_5$ is hydrogen or $R_4$.

$R_2$ is selected from the groups shown below, and the corresponding N-oxides thereof.

Heteroaryl or Heterocycloalkyl wherein K is O, S, SO, $SO_2$, or $CH_2$

The preferred novel compounds of formula (I) that form part of this invention, are as follows.

The following compounds 1 to 78 (named as per IUPAC or CAS nomenclature) are preferred compounds of formula (I) of the invention.

1. (S)-N-[[3-(3-fluoro-4-morpholinylphenyl)-2-oxo-5-oxazolidinyl]methyl]-4-oxo-4-phenylbutanamide.
2. (S)-N-[[3-(3-fluoro-4-morpholinylphenyl)-2-oxo-5-oxazolidinyl]methyl]-4-(4-methylphenyl)-4-oxobutanamide.
3. (S)-N-[[3-(3-fluoro-4-benzylpiperazinyl)phenyl]-2-oxo-5-oxazolidinyl]methyl]-4-oxo-4-phenylbutanamide.
4. (S)-N-[[3-(3-fluoro-4-[methylbenzylamino]phenyl)-2-oxo-5-oxazolidinyl]methyl]-4-(4-methyl phenyl)-4-oxobutanamide.
5. (S)-N-[[3-(3-fluoro-4-benzotriazolylphenyl)-2-oxo-5-oxazolidinyl]methyl]-4-oxo-4-phenylbutanamide.
6. (S)-N-[[3-(3-fluoro-4-pyrrolidinylphenyl)-2-oxo-5-oxazolidinyl]methyl]-4-oxo-4-phenylbutanamide.
7. (S)-N-[[3-(3-fluoro-4-benzotriazolylphenyl)-2-oxo-5-oxazolidinyl]methyl]-4-(4-methlyphenyl)-4-oxobutanamide.
8. (S)-N-[[3-(3-fluoro-4-thiomorpholinylphenyl)-2-oxo-5-oxazolidinyl]methyl]-4-oxo-4-phenylbutanamide.
9. (S)-N-[[3-(3-fluoro-4-benzylpiperazinyl)phenyl]-2-oxo-5-oxazolidinyl]methyl]-4-(4-methylphenyl)-4-oxobutanamide.
10. (S)-N-[[3-(3-fluoro-4-piperidylphenyl)-2-oxo-5-oxazolidinyl]methyl]-4-oxo-4-phenylbutanamide.
11. (S)-N-[[3-(3-fluoro-4-piperidylphenyl)-2-oxo-5-oxazolidinyl]methyl]-4-(4-methylphenyl)-4-oxobutanamide.

12. (S)-N-[[3-(3-fluoro-4-pyrrolidinylphenyl)-2-oxo-5-oxazolidinyl]methyl]-4-(4-methylphenyl)-4-oxobutanamide.
13. (S)-N-[[3-(3-fluoro-4-morpholinylphenyl)-2-oxo-5-oxazolidinyl]methyl]-4-(4-methoxyphenyl)-4-oxobutanamide.
14. (S)-N-[[3-(3-fluoro-4-morpholinylphenyl)-2-oxo-5-oxazolidinyl]methyl]-4-(4-chlorophenyl)-4-oxobutanamide.
15. (S)-N-[[3-(3-fluoro-4-morpholinylphenyl)-2-oxo-5-oxazolidinyl]methyl]-4-(4-methyl phenyl)-4-thiooxobutanamide.
16. (S)-N-[[3-(3-fluoro-4-morpholinylphenyl)-2-oxo-5-oxazolidinyl]methyl]-4-(4-2-naphthyl)-4-oxobutanamide.
17. (S)-N-[[3-(3-fluoro-4-morpholinylphenyl)-2-oxo-5-oxazolidinyl]methyl]-4-[4-(2'-methyl-4-propylphenyl)-4-oxobutanamide.
18. (S)-N-[[3-(3-fluoro-4-morpholinylphenyl)-2-oxo-5-oxazolidinyl]methyl]-4-(2,4-difluorophenyl)-4-oxobutanamide.
19. (S)-N-[[3-(3-fluoro-4-morpholinylphenyl)-2-oxo-5-oxazolidinyl]methyl]-4-oxo-4-(2-thienyl)butanamide.
20. (S)-N-[[3-(3-fluoro-4-morpholinylphenyl)-2-oxo-5-oxazolidinyl]methyl]-4-[4-(2',2'-dimethyl-4-ethylphenyl)-4-oxobutanamide.
21. (S)-N-[[3-(3-fluoro-4-morpholinylphenyl)-2-oxo-5-oxazolidinyl]methyl]-4-oxo-4-(4-thiomethyl)phenylbutanamide.
22. (S)-N-[[3-(3-fluoro-4-[methylbenzylamino]phenyl)-2-oxo-5-oxazolidinyl]methyl]-4-(4-methoxyphenyl)-4-oxobutanamide.
23. (S)-N-[[3-(3-fluoro-4-[methylbenzylamino]phenyl)-2-oxo-5-oxazolidinyl]methyl]-4-(2',2'-dimethyl-4-ethylphenyl)-4-oxobutanamide.
24. (S)-N-[[3-(3-fluoro-4-[methylbenzylamino]phenyl)-2-oxo-5-oxazolidinyl]methyl]-4-(2,4-dimethylphenyl)-4-oxobutanamide.
25. (S)-N-[[3-(3-fluoro-4-morpholinylphenyl)-2-oxo-5-oxazolidinyl]methyl]-4-(2,4-dimethylphenyl)-4-oxobutanamide.
26. (S)-N-[[3-(3-fluoro-4-pyrrolidinylphenyl)-2-oxo-5-oxazolidinyl]methyl]-4-(2,4-dimethylphenyl)-4-oxobutanamide.
27. (S)-N-[[3-(3-fluoro-4-benzotriazolylphenyl)-2-oxo-5-oxazolidinyl]methyl]-4-(2,4-dimethylphenyl)-4-oxobutanamide.
28. (S)-N-[[3-(3-fluoro-4-pyrrolidinylphenyl)-2-oxo-5-oxazolidinyl]methyl]-4-oxo-4-(2-thienyl)butanamide.
29. (S)-N-[[3-(3-fluoro-4-benzotriazolylphenyl)-2-oxo-5-oxazolidinyl]methyl]-4-oxo-4-(2-thienyl)butanamide.
30. (S)-N-[[3-(3-fluoro-4-morpholinylphenyl)-2-oxo-5-oxazolidinyl]methyl]-4-(4-2-naphthyl)-4-oxobutanamide-N-oxide.
31. (S)-N-[[3-(3-fluoro-4-morpholinylphenyl)-2-oxo-5-oxazolidinyl]methyl]-4-oxo-4-(2-thienyl)butanamide-N-oxide.
32. (S)-N-[[3-(3-fluoro-4-morpholinylphenyl)-2-oxo-5-oxazolidinyl]methyl]-4-(4-chlorophenyl)-4-oxobutanamide-N-oxide.
33. (S)-N-[[3-(3-fluoro-4-morpholinylphenyl)-2-oxo-5-oxazolidinyl]methyl]-4-[4-(2'-methyl-4-propylphenyl)-4-oxobutanamide-N-oxide.
34. (S)-N-[[3-(3-fluoro-4-morpholinylphenyl)-2-oxo-5-oxazolidinyl]methyl]-4-oxo-4-phenylbut-2-enamide.
35. (S)-N-[[3-(3-fluoro-4-piperidylphenyl)-2-oxo-5-oxazolidinyl]methyl]-4-(4-methoxyphenyl)-4-oxobutanamide.
36. (S)-N-[[3-(3-fluoro-4-piperidylphenyl)-2-oxo-5-oxazolidinyl]methyl]-4-(4-chlorophenyl)-4-oxobutanamide.
37. (S)-N-[[3-(3-fluoro-4-piperidylphenyl)-2-oxo-5-oxazolidinyl]methyl]-4-(2,4-dimethylphenyl)-4-oxobutanamide.
38. (S)-N-[[3-(3-fluoro-4-benztriazolylphenyl)-2-oxo-5-oxazolidinyl]methyl]-4-(4-methoxyphenyl)-4-oxobutanamide.
39. (S)-N-[[3-(3-fluoro-4-benzotriazolylphenyl)-2-oxo-5-oxazolidinyl]methyl]-4-(4-chlorophenyl)-4-oxobutanamide.
40. (S)-N-[[3-(3-fluoro-4-(1,2,4-triazolyl)phenyl)-2-oxo-5-oxazolidinyl]methyl]-4-oxo-4-phenylbutanamide.
41. (S)-N-[[3-(3-fluoro-4-(1,2,4-triazolyl)phenyl)-2-oxo-5-oxazolidinyl]methyl]-4-(4-methylphenyl)-4-oxobutanamide.
42. (S)-N-[[3-(3-fluoro-4-(1,2,4-triazolyl)phenyl)-2-oxo-5-oxazolidinyl]methyl]-4-(4-methoxyphenyl)-4-oxobutanamide.
43. (S)-N-[[3-(3-fluoro-4-(1,2,4-triazolyl)phenyl)-2-oxo-5-oxazolidinyl]methyl]-4-(2,4-dimethylphenyl)-4-oxobutanamide.
44. (S)-N-[[3-(3-fluoro-4-(1,2,4-triazolyl)phenyl)-2-oxo-5-oxazolidinyl]methyl]-4-oxo-4-(4-thiomethylphenyl)butanamide.
45. (S)-N-[[3-(3-fluoro-4-(1,2,4-triazolyl)phenyl)-2-oxo-5-oxazolidinyl]methyl]-4-(2',2'-dimethyl-4-ethylphenyl)-4-oxobutanamide.
46. (S)-N-[[3-(3-fluoro-4-(1,2,4-triazolyl)phenyl)-2-oxo-5-oxazolidinyl]methyl]-4-(2'-methyl-4-propylphenyl)-4-oxobutanamide.
47. (S)-N-[[3-(3-fluoro-4-(1,2,4-triazolyl)phenyl)-2-oxo-5-oxazolidinyl]methyl]-4-oxo-4-(2-thienyl)butanamide.
48. (S)-N-[[3-(3-fluoro-4-(1,2,4-triazolyl)phenyl)-2-oxo-5-oxazolidinyl]methyl]-4-(2-naphthyl)-4-oxobutanamide.
49. (S)-N-[[3-(3-fluoro-4-(1,2,4-triazolyl)phenyl)-2-oxo-5-oxazolidinyl]methyl]-4-(4-chlorophenyl)-4-oxobutanamide.
50. (S)-N-[[3-(3-fluoro-4-(1,2,4-triazolyl)phenyl)-2-oxo-5-oxazolidinyl]methyl]-4-(4-acetamidophenyl)-4-oxobutanamide.
51. (S)-N-[[3-(3-fluoro-4-(1,2,4-triazolyl)phenyl)-2-oxo-5-oxazolidinyl]methyl]-4-(2,4-difluorophenyl)-4-oxobutanamide.
52. (S)-N-[[3-(3-fluoro-4-piperidylphenyl)-2-oxo-5-oxazolidinyl]methyl]-4-oxo-4-(2-thienyl)butanamide.
53. (S)-N-[[3-(3-fluoro-4-piperidylphenyl)-2-oxo-5-oxazolidinyl]methyl]-4-(2'-methyl-4-propylphenyl)-4-oxobutanamide.
54. (S)-N-[[3-(3-fluoro-4-piperidylphenyl)-2-oxo-5-oxazolidinyl]methyl]-4-(4-acetamidophenyl)-4-oxobutanamide.
55. (S)-N-[[3-(3-fluoro-4-piperidylphenyl)-2-oxo-5-oxazolidinyl]methyl]-4-oxo-4-phenylbut-2-enamide.
56. (S)-N-[[3-(3-fluoro-4-pyrrolidinylphenyl)-2-oxo-5-oxazolidinyl]methyl]-4-oxo-4-(4-thiomethylphenyl)butanamide.
57. (S)-N-[[3-(3-fluoro-4-pyrrolidinylphenyl)-2-oxo-5-oxazolidinyl]methyl]-4-(2-naphthyl)-4-oxobutanamide.
58. (S)-N-[[3-(3-fluoro-4-pyrrolidinylphenyl)-2-oxo-5-oxazolidinyl]methyl]-4-(2'-methyl-4-propylphenyl)-4-oxobutanamide.
59. (S)-N-[[3-(3-fluoro-4-pyrrolidinylphenyl)-2-oxo-5-oxazolidinyl]methyl]-4-(2',2'-dimethyl-4-ethylphenyl)-4-oxobutanamide.
60. (S)-N-[[3-(3-fluoro-4-pyrrolidinylphenyl)-2-oxo-5-oxazolidinyl]methyl]-4-(4-acetamidophenyl)-4-oxobutanamide.

61. (S)-N-[[3-(3-fluoro-4-pyrrolidinylphenyl)-2-oxo-5-oxazolidinyl]methyl]-4-oxo-4-phenylbut-2-enamide.
62. (S)-N-[[3-(3-fluoro-4-thiomorpholinylphenyl)-2-oxo-5-oxazolidinyl]methyl]-4-(4-methoxyphenyl)-4-oxobutanamide.
63. (S)-N-[[3-(3-fluoro-4-thiomorpholinylphenyl)-2-oxo-5-oxazolidinyl]methyl]-4-(2,4-dimethylphenyl)-4-oxobutanamide.
64. (S)-N-[[3-(3-fluoro-4-thiomorpholinylphenyl)-2-oxo-5-oxazolidinyl]methyl]-4-oxo-4-(2-thienyl)butanamide.
65. (S)-N-[[3-(3-fluoro-4-thiomorpholinylphenyl)-2-oxo-5-oxazolidinyl]methyl]-4-(4-acetamidophenyl)-4-oxobutanamide.
66. (S)-N-[[3-(3-fluoro-4-piperidylphenyl)-2-oxo-5-oxazolidinyl]methyl]-4-oxo-4-(4-thiomethylphenyl)butanamide.
67. (S)-N-[[3-(3-fluoro-4-piperidylphenyl)-2-oxo-5-oxazolidinyl]methyl]-4-(2-naphthyl)-4-oxobutanamide.
68. (S)-N-[[3-(3-fluoro-4-piperidylphenyl)-2-oxo-5-oxazolidinyl]methyl]-4-(2',2'-dimethyl-4-ethylphenyl)-4-oxobutanamide.
69. (S)-N-[[3-(3-fluoro-4-benzotriazolylphenyl)-2-oxo-5-oxazolidinyl]methyl]-4-oxo-4-(4-thiomethylphenyl)butanamide.
70. (S)-N-[[3-(3-fluoro-4-benzotriazolylphenyl)-2-oxo-5-oxazolidinyl]methyl]-4-(2-naphthyl)-4-oxobutanamide.
71. (S)-N-[[3-(3-fluoro-4-benzotriazolylphenyl)-2-oxo-5-oxazolidinyl]methyl]-4-(2',2'-dimethyl-4-ethylphenyl)-4-oxobutanamide.
72. (S)-N-[[3-(3-fluoro-4-benzotriazolylphenyl)-2-oxo-5-oxazolidinyl]methyl]-4-oxo-4-phenylbut-2-enamide.
73. (S)-N-[[3-(3-fluoro-4-benzotriazolylphenyl)-2-oxo-5-oxazolidinyl]methyl]-4-(4-acetamidophenyl)-4-oxobutanamide.
74. (S)-N-[[3-(3-fluoro-4-thiomorpholinylphenyl)-2-oxo-5-oxazolidinyl]methyl]-4-(2',2'-dimethyl-4-ethylphenyl)-4-oxobutanamide.
75. (S)-N-[[3-(3-fluoro-4-thiomorpholinylphenyl)-2-oxo-5-oxazolidinyl]methyl]-4-oxo-4-phenylbut-2-enamide.
76. (S)-N-[[3-(3-fluoro-4-thiomorpholinylphenyl)-2-oxo-5-oxazolidinyl]methyl]-4-(2-naphthyl)-4-oxobutanamide.
77. (S)-N-[[3-(3-fluoro-4-thiomorpholinylphenyl)-2-oxo-5-oxazolidinyl]methyl]-4-(4-chlorophenyl)-4-oxobutanamide.
78. (S)-N-[[3-(3-fluoro-4-thiomorpholinylphenyl)-2-oxo-5-oxazolidinyl]methyl]-4-(2,4-dimethyl-4 ethylphenyl)-4-oxobutanamide.

The respective N-oxides of the group $R_2$ of the compounds of formula I listed above also form a novel aspect of the present invention.

The pharmaceutically active compounds of formula (I), the corresponding N-oxides of the group $R_2$ and pharmaceutically acceptable salts thereof of this invention can be prepared by methods known to one skilled in the art.

Typically, compounds of formula (I), can be prepared by coupling of the amino fragment of formula (II)

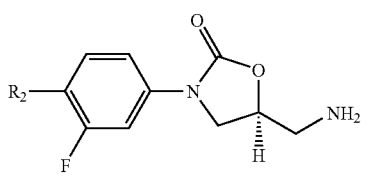

(II)

with the carboxylic acid fragment of formula (III)

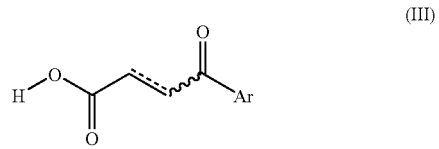

(III)

The coupling reaction is carried out by any of the various standard peptide bond forming techniques as disclosed for example in, "*The peptides. Analysis, Synthesis, Biology, Vol. 1, Major Methods of Peptide Bond Formation, Part A*", E. Gross and J. Meierhofer Ed., Academic Press N.Y. (1979). An especially useful method involves the use of a dehydrating agent, such as dicyclohexylcarbodiimide (DCC) alone or in the presence of reagents forming reactive esters, e.g., 1-hydroxybenztriazole (HOBt), in a suitable solvent selected from dimethylformamide, acetonitrile, tetrahydrofuran or chlorinated hydrocarbons mixed with water.

The N-oxides of compounds of formula (I) thus obtained are prepared by standard methods known in the art, for example by oxidation of compounds of formula (I) with a an oxidizing agent as per the general procedure disclosed in WO 97/10223 (Gadwood et. al.). A preferred method of oxidation is through utilization of m-chloro perbenzoic acid (m-CPBA) in a suitable solvent, specially chlorinated hydrocarbons.

A schematic representation of the method for preparation of compound of formula (I) and its N-oxide thereof is summarized in Scheme-I.

Scheme-I
General method for synthesis of compounds of formula (I)

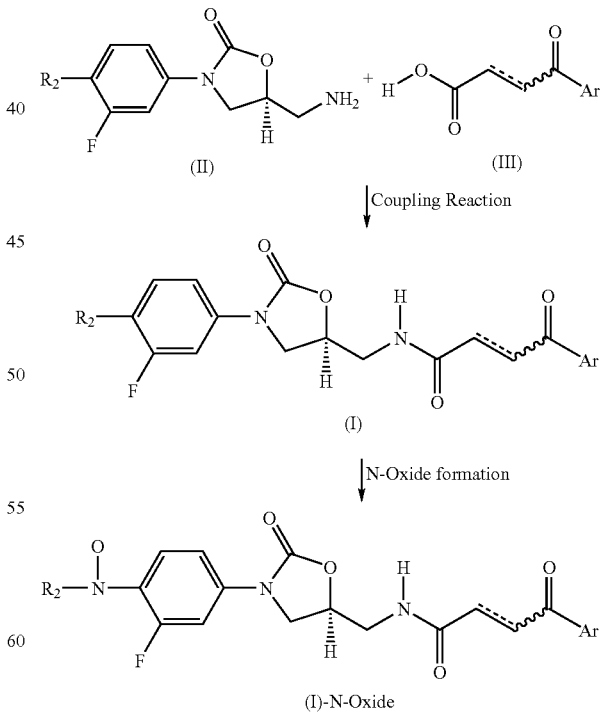

In a typical experiment, the amine compound of formula (II), wherein the groups A, B, and $R_2$ have the same meanings as defined hereinbefore is dissolved in a 1:1 mixture of tertahydrofuran and water or a 1:1 mixture of methylene chloride and water. To the solution is added the carboxylic acid compound of formula (III), followed by addition of 1-hydroxybenztriazole (HOBt). The resulting mixture is cooled to a temperature of 0-5° C. to which 1-(3-dimethylaminopropyl)-3-ethylcarbodiimide hydrochloride, 1.1 Eq.) is added and gradually allowed to warm to room temperature and agitated at this temperature for 24 hours. At the end of the reaction, a solution of saturated aqueous sodium bicarbonate is added and the organic phase separated from the aqueous phase. Evaporation of the solvent and chromatography of the residue over silica gel affords compound of formula (I), generally as white solids.

The N-oxides of the group $R_2$ of compound of formula (I) thus obtained are preferably prepared by addition of m-chloro perbenzoic acid (m-CPBA) to a cooled solution of the compound of formula (I) in a chlorinated hydrocarbon solvent such as methylene chloride and ethylene chloride and thereafter agitating the reaction mixture at room temperature for 12-15 hours. Evaporation of the solvent under reduced pressure, followed by chromatography of the residue over silica gel affords the corresponding N-oxides in high purity.

The N-oxides thus prepared, while retaining most of the antimycobacterial activity of the corresponding deoxo compound exhibit exceedingly high water solubility over the deoxo analogue, thereby helping in manufacture of suitable iv formulations, which forms an important aspect of this invention.

The starting materials required for synthesis of compound of formula (I), thus involve the amine compound of formula II and the carboxylic acid compound of formula III.

The amine compound of formula II can be selected from i) (S)-N-[3-(3-fluoro-4-morpholinylphenyl)-2-oxo-5-oxazolidinyl]methyl amine, ii) (S)-N-[3-(3-fluoro-4-thiomorpholinylphenyl)-2-oxo-5-oxazolidinyl]methyl amine, iii) (S)-N-[3-(3-fluoro-4-piperidylphenyl)-2-oxo-5-oxazolidinyl]methyl amine, iv) (S)-N-[3-(3-fluoro-4-benzylpiperazinylphenyl)-2-oxo-5-oxazolidinyl]methyl amine, v) (S)-N-[3-(3-fluoro-4-pyrrolidinylphenyl)-2-oxo-5-oxazolidinyl]methyl amine, vi) (S)-N-[3-(3-fluoro-4-(1,2,4-triazolyl)phenyl)-2-oxo-5-oxazolidinyl]methyl amine, vii) (S)-N-[3-(3-fluoro-4-benzotriazolylphenyl)-2-oxo-5-oxazolidinyl]methyl amine, and viii) (S)-N-[3-(3-fluoro-4-[methylbenzylamino]phenyl)-2-oxo-5-oxazolidinyl]methyl amine.

The Representative Amines of Formula (II)

1.

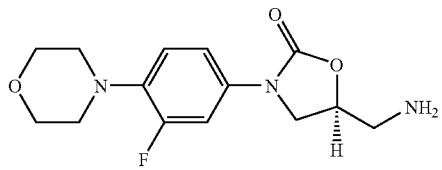

2.

3.

4.

5.

6.

7.

8.

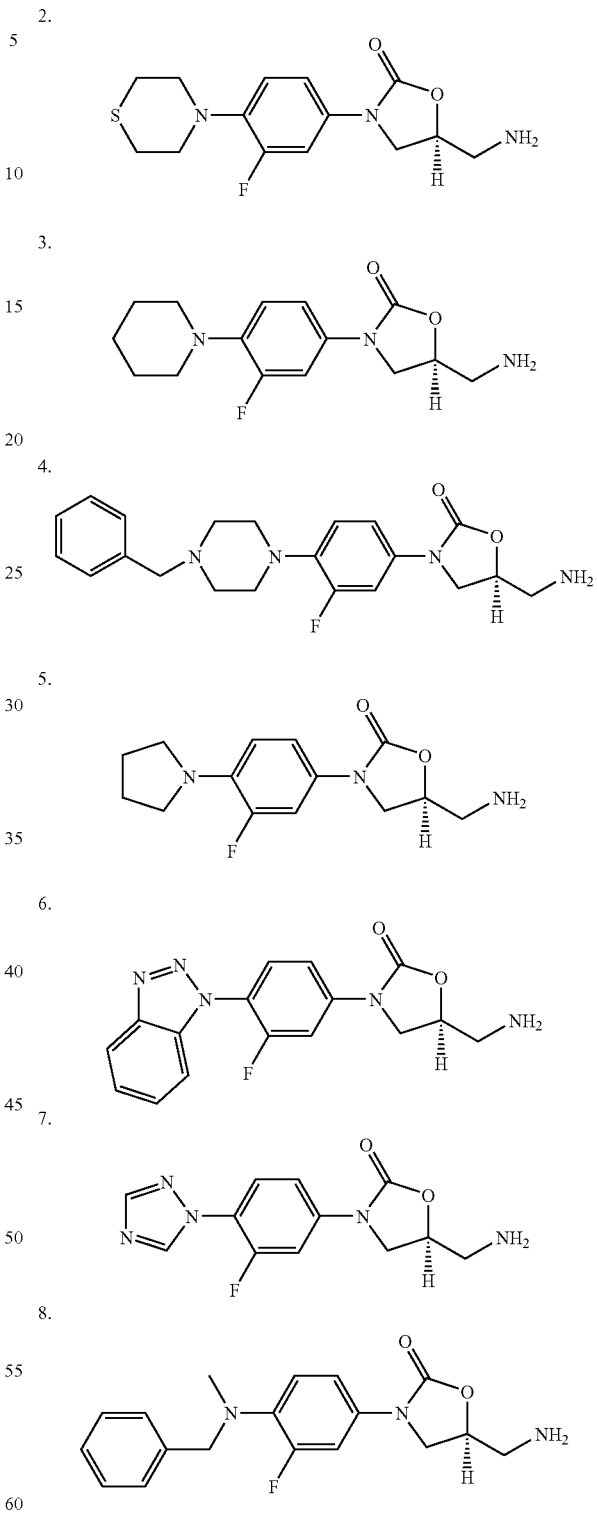

The carboxylic acid compound of formula III can be selected from 4-(2-Naphthyl)-4-oxobutanoic acid, 4-Oxo-4-(2-Thienyl)butanoic acid, 4-Oxo-4-(4-thiomethyl)phenylbutanoic acid, 4-oxo-4-(2'methylpropyl)phenylbutanoic acid, 4-Oxo-4-(2',2'dimethylethyl)phenylbutanoic acid, 4-(4-methylphenyl)-4-oxobutanoic acid, 4-(2,4-dimethylphenyl)-4- oxobutanoic acid, 4-(4-methoxyphenyl)-4-oxobutanoic acid, 4-(4-chlorophenyl)-4-oxobutanoic acid, 4-(2,4-dichlorophenyl)-4-oxobutanoic acid, 4-(2,4-difluorophenyl)-4-oxobutanoic acid, 4-(2-Naphthyl)-4-oxobutanoic acid, 4-(4-acetamidophenyl)-4-oxobutanoic acid, (2 E/Z)-Oxo-4-phenylbut-2-enoic acid, and 4-oxo-4-phenyl-but-2-ynoic acid.

The Representative Carboxylic Acids of Formula (III)

1. 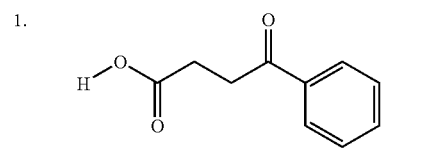

2. 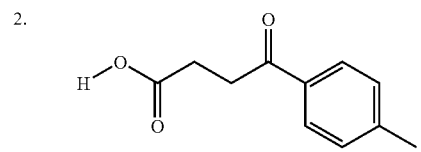

3. 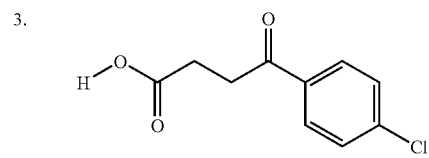

4. 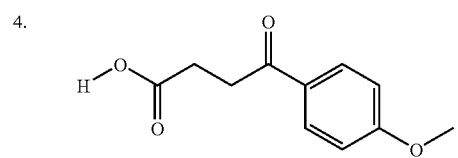

5. 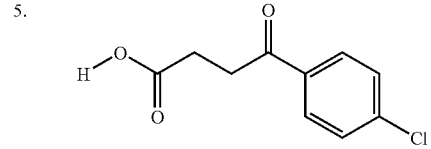

6. 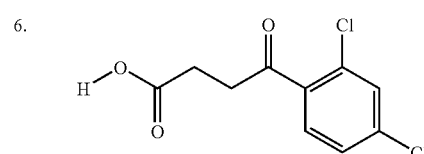

7. 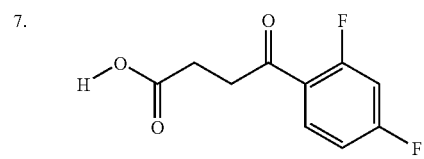

-continued

8. 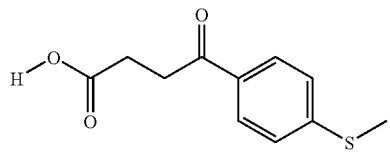

9. 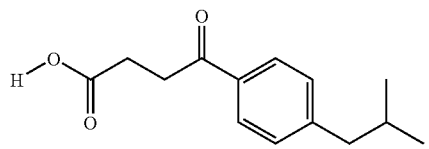

10. 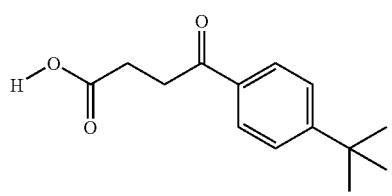

11. 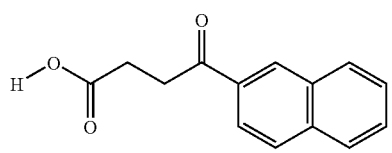

12. 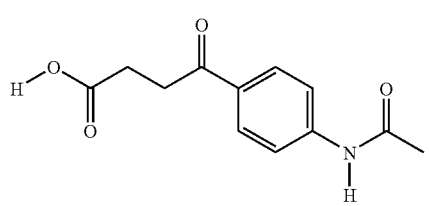

13. 

14. 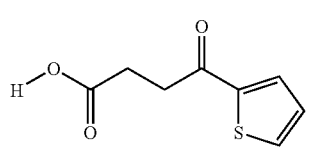

15. 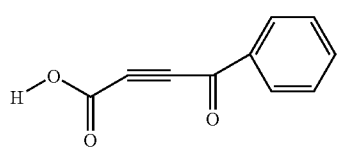

Thus, the starting amines of formula (II), wherein the groups A, B, and $R_2$ have the same meanings as defined hereinearlier are prepared as per the method disclosed by W. A. Gregory et. al., *J. Med. Chem.*, 1989, 32, 1673-1681 and 1990, 33, 2569-2578; C. Wang et. al., *Tetrahedron*, 1989, 45, 1323-1326; Britelli et. al., *J. Med. Chem.*, 1992, 35, 1156 and *Bioorg. Med. Chem. Lett.*, 1999, 9, 2679-2684; M. R. Barbachyn et. al., *J. Med. Chem.*, 1996, 39, 680-685; M. J. Genin et. al., *J. Med. Chem.*, 2000, 43, 953-970; WO 95/25106 and WO 97,21708. The method is essentially summarized in Scheme-II.

Scheme-II
General method for synthesis of amines of formula (II)

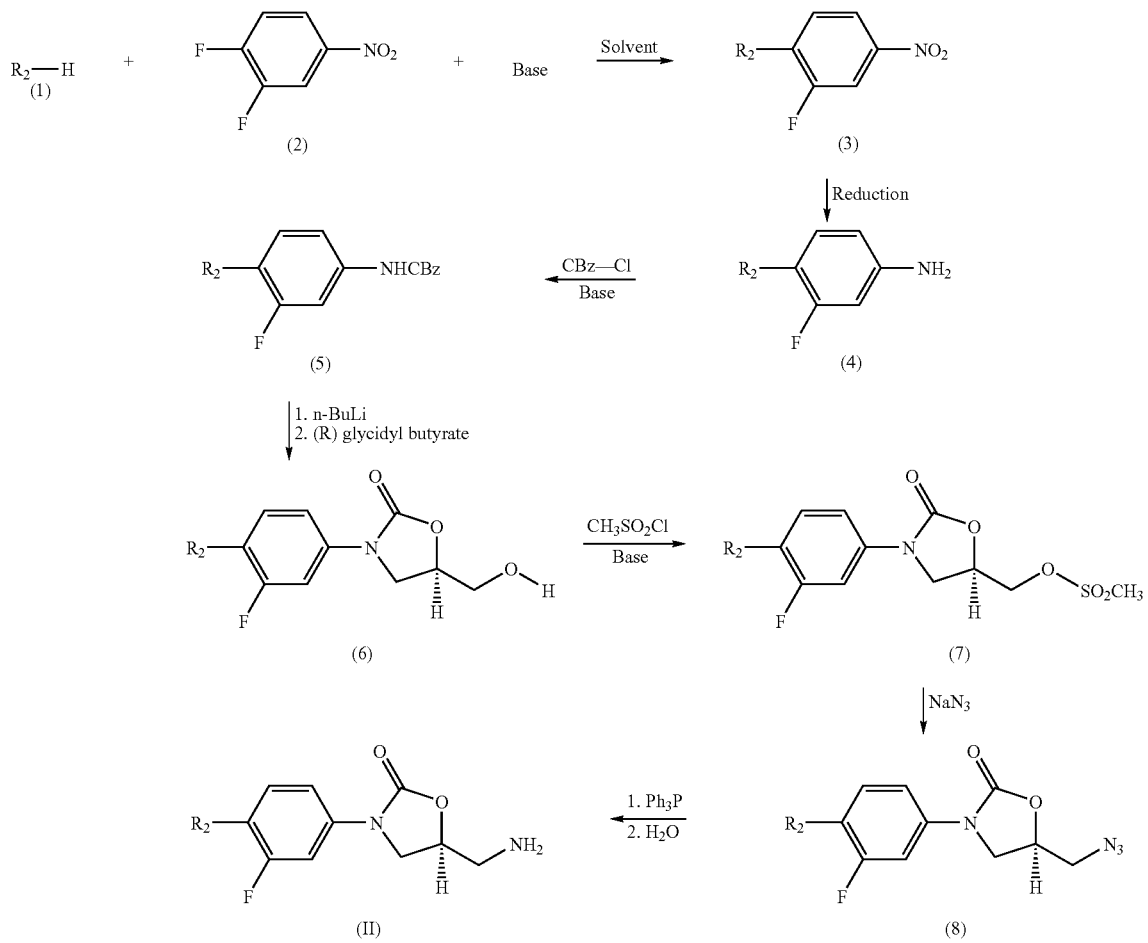

In a typical method, morpholine, thiomorpholine, piperidine, 4-benzyl piperazine, pyrrolidine, 1,2,4-triazine, 12,3-benzotriazine, benzyl amine, a heterocycloalkyl or a heteroaryl moiety etc., each one of which corresponds to the group $R_2$ defined hereinbefore is reacted with 3,4-difluoro nitrobenzene in the presence of a base and a solvent to give the corresponding derivative in which the fluorine atom at 4-position is substituted by the group $R_2$. The nitro group in the compound thus obtained is reduced to amino group, which is thereafter protected by a suitable protective group. Reaction of the N-protected compound thus obtained with (R)-glycidyl butyrate in the presence of a strong base like n-butyl lithium leads to formation of the 5-hydroxymethyl oxazolidinone ring. The hydroxy group in the compound thus obtained is converted to sulfonyl derivative, for e.g. a methanesulfonyloxy (mesyl) or a p-toluenesulfonyloxy (tosyl) derivative by reaction with methanesulfonyl chloride or p-toluenesulfonyl chloride respectively. Reaction of the respective mesyl or tosyl derivative with sodium azide gives the corresponding azide, which is converted to the amine compound of formula (II) by standard methods, for e.g. by reaction with a triaryl/trialkyl phosphine, followed by hydrolysis.

The starting carboxylic acid fragments of formula (III), wherein the group Ar has the same meaning as defined hereinearlier are prepared as per the method disclosed in *Org. Reactions,* 1949, 5, 229-289; *Quart. Rev. Chem. Soc.,* 1954, 8, 355-379; *Chem. Rev.,* 1955, 55, 229-281, and *J. Am. Chem. Soc.,* 1947, 69, 1784-1786. The method is essentially summarized in Scheme-III.

Scheme-III
General method for synthesis of alkane and alkene carboxylic acid s of formula (III)

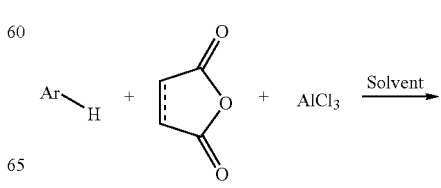

-continued

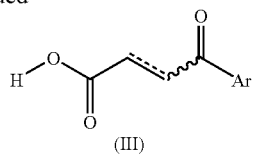

In a typical method, the aromatic compound Ar—H, wherein Ar is as defined hereinbefore is reacted with succinic anhydride in the presence of a Lewis acid, such as anhydrous aluminium chloride and in the presence of an anhydrous solvent and the mixture heated to 100° C. to give the carboxylic acid derivatives of formula (III), wherein Q is alkyl of 1-4 carbon atoms.

Similarly, compounds of formula (III), wherein Q is an alkene (CH═CH) are prepared by reaction of the aromatic compound Ar—H, wherein Ar is as defined hereinbefore with maleic anhydride under the same conditions mentioned hereinbefore.

Compounds of formula (III), wherein Q is an alkyne (C≡C) are prepared by reaction of propiolic acid ester with an aldehyde of formula Ar—CHO in the presence of butyl lithium and in the presence of an aprotic solvent such as THF at −78° C. to give the corresponding secondary alcohol, which is oxidized to the keto derivative using manganese dioxide as the oxidizing agent. Saponification gives the carboxylic acid derivative of formula (III) [U.S. Pat. No. 4,929,741 (A. Fischili et. al.)] The synthesis is summarized in Scheme-IV.

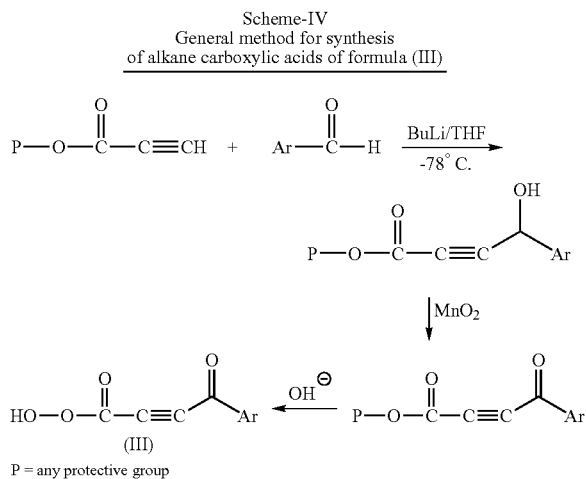

The synthesis of compound of formula (I) of this invention and the synthesis of the respective starting material amines of formula (II) and the carboxylic acids of formula (III) are further described herein in detail.

Synthesis of the Starting Amines of Formula (II)

The amines were prepared as per the chemistry summarized in the Scheme-II and as per the methods disclosed by W. A. Gregory et. al., *J. Med. Chem.,* 1989, 32, 1673-1681 and 1990, 33, 2569-2578; C. Wang et. al., *Tetrahedron,* 1989, 45, 1323-1326; Britelli et. al., *J. Med. Chem.,* 1992, 35, 1156 and *Bioorg. Med. Chem. Lett.,* 1999, 9, 2679-2684; M. R. Barbachyn et. al., *J. Med. Chem.,* 1996, 39, 680-685; M. J. Genin et. al., *J. Med. Chem.,* 2000, 43, 953-970; WO 95/25106 and WO 97,21708. Commercially available raw materials and known techniques were utilized for the synthesis.

The optically pure amines as such were obtained by using optically active intermediates or resolution of racemic mixtures by a suitable reagent. The preferred enantiomer is (S), at the chiral centre on the oxazolidinone ring.

EXAMPLE 1

General Method for Preparation of the Amines (II)

The oxazolidinone azides of general formula (8), given in Scheme-II (1.0 eq) were dissolved in dry THF (10 times by volume) and treated with triphenyl phosphine (1.5 eq.) at room temp. The resulting solution was stirred for 6 hrs at room temp. Water [2 eq. of (8)] was added and the solution heated for 6 hrs at 55-60° C. The solvent was evaporated and the residue chromatographed on a column of silica gel (100-200 mesh) and eluted initially with ethyl acetate and then with chloroform:methanol (4:1) to give the amines (II) as white solids.

The following amines i) to viii) of formula I were prepared by this general method, viz.
i) (S)-N-[3-(3-fluoro-4-morpholinylphenyl)-2-oxo-5-oxazolidinyl]methyl amine,
ii) (S)-N-[3-(3-fluoro-4-thiomorpholinylphenyl)-2-oxo-5-oxazolidinyl]methyl amine,
iii) (S)-N-[3-(3-fluoro-4-piperidylphenyl)-2-oxo-5-oxazolidinyl]methyl amine,
iv) (S)-N-[3-(3-fluoro-4-benzylpiperazinylphenyl)-2-oxo-5-oxazolidinyl]methyl amine,
v) (S)-N-[3-(3-fluoro-4-pyrrolidinylphenyl)-2-oxo-5-oxazolidinyl]methyl amine,
vi) (S)-N-[3-(3-fluoro-4-(1,2,4-triazolyl)phenyl)-2-oxo-5-oxazolidinyl]methyl amine,
vii) (S)-N-[3-(3-fluoro-4-benzotriazolylphenyl)-2-oxo-5-oxazolidinyl]methyl amine, and
viii) (S)-N-[3-(3-fluoro-4-[methylbenzylamino]phenyl)-2-oxo-5-oxazolidinyl]methyl amine.

Synthesis of the Starting Carboxylic Acids of Formula (III)

EXAMPLE 2

4-(2-Naphthyl)-4-oxobutanoic acid

Naphthalene (5.0 gm, 0.039 moles) and succinic anhydride (4.68 gm, 0.0468 moles) were taken up in dichloroethane (50 ml). Aluminium chloride (11.44 g, 0.0858 moles) was added at room temperature and the resulting mixture heated under reflux for 1 hr with stirring. The reaction mixture was cooled to room temperature, diluted with 25 ml of 1:1 mixture of water and Conc. hydrochloric acid. After stirring for 10 min the separated solid was filtered under suction, washed with water and dilute hydrochloric acid. Subsequent column chromatography gave a buff coloured solid. Subsequent chromatography gave 3.7 gm (41%) the title compound, mp 173-174° C.

$^1$H NMR (CDCl$_3$, δ): 8.40 (s,1H), 7.7-8.0 (m, 4H), 7.4-7.6 (m,2H), 3.33 (t,2H), 2.77 (t,2H+1H).

The filterate was concentrated to give 5.8 gm of a mixture of 4-(2-naphthyl)-4-oxobutanoic and 4-(1-naphthyl)-4-oxobutanoic acid.

EXAMPLE 3

4-Oxo-4-(2-Thienyl)butanoic acid

Thiophene (5.0 gm, 0.059 moles) and succinic anhydride (7.13 gm, 0.0713 moles) were taken up in dichloroethane (50 ml). Aluminium chloride (17.43 gm, 0.131 moles) was added at room temperature and the resulting mixture heated under reflux for 1 hr with stirring. The reaction mixture was cooled to room temperature, diluted with 30 ml of 1:1 mixture of water and Conc. hydrochloric acid. After stirring for 10 min the separated solid was filtered under suction, washed with water and dilute hydrochloric acid (50 ml). The solid was dried at room temp to give 9.8 gm (89%0 of the title compound, mp 103-107° C.

$^1$H NMR (CDCl$_3$, δ): 7.69 (dd, 1H), 7.58 (dd,1H), 7.07 (dd,1H), 3.9 (bs, 1H), 3.23 (t, 2H), 2.74 (t,2H).

EXAMPLE 4

4-Oxo-4-(4-thiomethyl)phenylbutanoic acid

Thiophenol methyl ether (8.0 gm, 0.0645 moles) and succinic anhydride (7.75 gm, 0.0774 moles) were taken up in dichloroethane (80 ml). Aluminium chloride (18.90 gm, 0.1419 moles) was added at room temperature. The resulting mixture stirred for 0.5 hr and then heated at 85° C. for 1 hr. The reaction mixture was cooled to room temperature, diluted with 40 ml of 1:1 mixture of water and Conc. hydrochloric acid. After stirring for 10 min the separated solid was filtered under suction, washed with water and dilute hydrochloric acid (80 ml). The solid was dried at room temp to give 6.9 gm (48%) of the title compound, mp 151-154° C.

$^1$H NMR (CDCl$_3$, δ): 7.82 (d,2H), 7.20 (d, 2H), 4.2 (bs, 1H), 3.21 (t, 2H), 2.73(t, 2H),2.45 (s,3H).

EXAMPLE 5

4-oxo-4-(2'methylpropyl)phenylbutanoic acid

2'methylpropylbenzene (5.0 m, 0.0373 moles) and succinic anhydride (4.5 gm, 0.0448 moles), were taken up in dichloroethane (50 ml). Aluminium chloride (10.90 g, 0.0821 moles) was added at room temperature and the mixture heated under reflux for 1 hr with stirring. The reaction mixture was cooled to room temperature, diluted with 40 ml of a 1:1 mixture of water and Conc. hydrochloric acid. After stirring for 10 min the reaction mixture was extracted with ethyl acetate (25 ml). The ethyl acetate layer was dried and concentrated to give 8.7 gm (99%) of the title compound as a solid, mp 102-105° C.

$^1$H-NMR (CDCl$_3$, δ): 7.83 (d,2H), 7.17(d,2H), 3.24(t,2H), 2.74(t, 2H), 2.46 (d, 2H), 1.80 (pent., 1H).

EXAMPLE 6

4-Oxo-4-(2',2'dimethylethyl)phenylbutanoic acid

2',2'dimethylethylbenzene (5.0 gm, 0.0373 moles) and succinic anhydride (4.5 gm, 0.0448 moles) were taken up in dichloroethane (50 ml). Aluminium chloride (10.90 gm, 0.0821 moles) was added at room temperature and the mixture heated under reflux for 1 hr with stirring. The reaction mixture was cooled to room temperature, diluted with 40 m of a 1:1 mixture of water Conc. hydrochloric acid. After stirring for 10 min the reaction mixture was extracted with ethyl acetate (25 ml). The ethyl acetate layer was dried and concentrated to give 8.5 gm (97%) of the title compound as a solid, mp 103-107° C.

$^1$H-NMR (CDCl$_3$, δ): 7.94(d,2H), 7.50 (d, 2H), 3.29 (t,2H), 2.82 (t,2H), 1.36 (s,9H).

EXAMPLE 7

Using the appropriate aromatic compound (Ar—H) and succinic anhydride and following exactly the method described in Examples 2-6 the following carboxylic acids can be prepared, viz.
i) 4-(4-methylphenyl)-4-oxobutanoic acid,
ii) 4-(2,4-dimethylphenyl)-4-oxobutanoic acid,
iii) 4-(4-methoxyphenyl)-4-oxobutanoic acid,
iv) 4-(4-chlorophenyl)-4-oxobutanoic acid,
v) 4-(2,4-dichlorophenyl)-4-oxobutanoic acid,
vi) 4-(2,4-difluorophenyl)-4-oxobutanoic acid,
vii) 4-(2-Naphthyl)-4-oxobutanoic acid,
viii) 4-(4-acetamidophenyl)-4-oxobutanoic acid,
ix) (2 E/Z)-Oxo-4-phenylbut-2-enoic acid, and
x) 4-oxo-4-phenyl-but-2-ynoic acid.

Synthesis of the Compounds of Formula (I)

EXAMPLE 7

Preparation of (S)-N-[[3-(3-fluoro-4-morpholinylphenyl)-2-oxo-5-oxazolidinyl]methyl]-4-(4-naphthyl)-4-oxobutanamide (S)-N-[3-(3-fluoro-4-morpholinylphenyl)-2-oxo-5-oxazolidinyl]methyl amine (0.200 gm, 0.00068 moles) was taken up in 1:1 dichloromethane-water mixture (10 ml). To this was added 4-(2-naphthyl-4-oxobutanoic acid (0.154 gm, 0.00068 moles and HOBt (0.091 gm, 0.00068 moles) the resulting mixture was cooled to 0° C. 1-(3-dimethylaminopropyl)-3-ethylcarbodiimide hydrochloride (0.142 gm, 0.00074 moles) was added the resulting mixture was allowed to warm to room temperature and then stirred for 24 hr. Saturated aqueous sodium bicarbonate solution (2 ml) was added to the reaction mixture, stirred for 15 min and then the organic layer separated and the solvent evaporated off. The residue was chromatographed over silica gel (100-200 mesh, 20 gm). The column was eluted with mixture of ethyl acetate: hexane, and finally with ethyl acetate. The combined fractions were concentrated to give the title compound (0.22 gm, 64%) as a white solid.

MS (M+1)=506 m/z $^1$H NMR (CDCl$_3$, δ): 8.35(s,1H),7.83 (m, 4H), 7.50(m, 2H),7.38 (dd, 1H), 7.01(dd,1H), 6.74 (t,1H), 6.41 (t,1H), 4.71(m,1H), 3.88 (t, 1H), 3.77 (m, 4H), 3.5-3.8 (m, 3H), 3.40 (dd, 2H), 2.91 (m,4H), 2.60(t, 2H).

EXAMPLE 8

Preparation of (S)-N-[[3-(3-fluoro-4-morpholinylphenyl)-2-oxo-5-oxazolidinyl]methyl]-4-oxo-4-(2-thienyl)butanamide (S)-N-[3-(3-fluoro-4-morpholinylphenyl)-2-oxo-5-oxazolidinyl]methyl amine (0.200 gm, 0.00068 moles) was taken up in 1:1 THF-water mixture (20 ml). To this was added 4-oxo-4 (2-thienyl)butanoic acid (0.125 gm, 0.00068 moles) and HOBt (0.091 gm, 0.00068 moles). The resulting mixture was cooled to 0° C. and then 1-(3-dimethylaminopropyl)-3-ethylcarbodiimide hydrochloride (0.142 gm, 0.00074 moles)

was added and the resulting mixture was allowed to warm to room temp and then stirred for 24 hr. The reaction mixture was concentrated, 15 ml of saturated sodium bicarbonate was added, stirred for 15 min and then extracted with ethyl acetate. The ethyl acetate layer was separated and the solvent evaporated off. The residue was chromatographed over silica gel (100-200 mesh, 20 gm). The column was eluted with mixture of ethyl acetate:hexane, and finally with ethyl acetate. The combined fractions were concentrated to give the title compound (0.175 gm, 56%) as a white solid.

MS (M+1)=462 m/z $^1$H NMR (CDCl$_3$, δ): 7.63(d,1H), 7.55 (dd,1H), 7.35(dd, 1H), 7.04(t, like dd, 2H), 6.83(t,1H), 6.30 (t,1H), 4.69(m,1H), 3.93 (t, 1H), 3.6-3.8 (m, 3H),3.80 (m,4H), 3.61(dd, 2H), 3.21(dd,2H),2.97 (m,4H),2.55(t, 2H).

EXAMPLE 9

Preparation of (S)-N-[[3-(3-fluoro-4-morpholinylphenyl)-2-oxo-5-oxazolidinyl]methyl]-4-[4-(2'-methyl-4-propylphenyl)-4-oxobutanamide (S)-N-[3-(3-fluoro-4-morpholinylphenyl)-2-oxo-5-oxazolidinyl]methyl amine (0.200 gm, 0.00068 moles) was taken up in 1:1 THF-water mixture (20 ml). To this was added 4-[4(2'-methylpropylphenyl)]-4-oxobutanoic acid (0.158 gm, 0.00068 moles and HOBt (0.091 gm, 0.00068 moles). The resulting mixture was cooled to 0° C., and then 1-(3-dimethylaminopropyl)-3-ethylcarbodiimide hydrochloride (0.142 gm, 0.00074 moles) was added and the mixture was allowed to warm to room temperature and then stirred for 24 hr. The reaction mixture was concentrated, 15 ml of saturated aqueous sodium bicarbonate solution was added, stirred for 15 min and then extracted with ethyl acetate. The ethyl acetate layer was separated, and evaporated off. The residue was chromatographed over silica gel (100-200 mesh, 20 g) and eluted with mixture of ethyl acetate:hexane, and finally with ethyl acetate. The combined fractions were concentrated to give the title compound (0.210 gm, 60%) as a white solid.

MS (M=1)=512 m/z $^1$H NMR (CDCl$_3$, δ): 7.73 (d,2H), 7.52 (dd,1H), 7.28(m, 1H),7.15 (d,2H), 7.05 (d,1H), 6.39 (t,1H), 4.75(m 1H), 3.91 (m, 4H), 3.5-3.9 (m, 4H), 3.28 (dd, 2H), 3.16 (m,4H),2.54 (t, 2H), 2.45 (d, 2H), 1.82 (pent., 1H), 2.60 (t, 2H).

EXAMPLE 10

Preparation of (S)-N [[3-(3-fluoro-4-morpholinylphenyl)-2-oxo-5-oxazolidinyl]methyl]-4-oxo-4-(4-thiomethyl)phenylbutanamide (S)-N-[3-(3-fluoro-4-morpholinylphenyl)-2-oxo-5-oxazolidinyl]methyl amine (0.200 gm, 0.00068 moles) was taken up in 1:1 THF-water mixture (20 ml). To this was added 4-(4-methlythiophenyl)-4-oxobutanoic acid (0.152 g, 0.00068 moles and HOBt (0.091 gm, 0.00068 moles) and the resulting mixture was cooled to 0° C., and then 1-(3-dimethylaminopropyl)-3-ethylcarbodiimide hydrochloride (0.142 g, 0.00074 moles) was added. The resulting mixture was allowed to warm to room temperature and then stirred for 24 hr. The reaction mixture was concentrated, 15 ml of saturated aqueous sodium bicarbonate was added to, stirred for 15 min and then extracted with ethyl acetate. The ethyl acetate layer was separated and evaporated off. The residue was chromatographed over silica gel (100-200 mesh, 20 g). The column was eluted with mixture of ethyl acetate:hexane, and finally with ethyl acetate. The combined fractions were concentrated to give the title compound (0.270 gm, 79%) as a white solid.

MS (M+1)=502 m/z $^1$H NMR (CDCl$_3$, δ): 7.70(d,2H), 7.37 (dd,1H), 7.14(d, 2H), 7.00 (dd,1H), 6.79(t,1H), 6.38 (t,1H), 4.71(m,1H), 3.86 (t,1H),3.5-3.9 (m, 4H), 3.81 (m, 4H), 3.22 (dd, 2H), 2.96 (m,4H), 2.53 (t, 2H), 2.45 (s, 3H).

EXAMPLE 11

Preparation of: (S)-N-[[3-(3-fluoro-4-morpholinylphenyl)-2-oxo-5-oxazolidinyl]methyl]-4-(4-chlorophenyl)-4-oxobutanamide (S)-N-[3-(3-fluoro-4-morpholinylphenyl)-2-oxo-5-oxazolidinyl]methyl amine (0.100 gm, 0.00034 moles) was taken up in 1:1 THF-water mixture (20 ml). To this was added 4-(4-chlorophenyl)-4-oxobutanoic acid (0.072 g, 0.00034 moles and HOBt (0.046 g, 0.00034 moles). The resulting mixture was cooled to 0° C., and then 1-(3-dimethylaminopropyl)-3-ethylcarbodiimide hydrochloride (0.071 gm, 0.00037 moles) was added. The resulting mixture was allowed to warm to room temperature and then stirred for 24 hr. The reaction mixture was concentrated and 2 ml of saturated aqueous sodium bicarbonate solution was added, stirred for 15 min and then extracted with dichloromethane. The organic layer was separated and evaporated off. The residue was chromatographed over silica gel (100-200 mesh, 20 g) and eluted with mixture of ethyl acetate:hexane, and finally with ethyl acetate. The combined fractions were concentrated to give (0.070 gm, 42%) of the title compound as a white solid.

MS (M+1)=490 m/z $^1$H NMR (CDCl$_3$, δ): 7.72(d,2H),7.37 (dd,1H),7.31(d,2H), 6.98 (dd,1H),6.79 (t,1H), 6.28 (t,1H), 4.69(m,1H), 3.83 (t, 1H), 3.81 (m, 4H), 3.4-3.m (m, 3H), 3.21 (dd, 2H), 2.97 (m,4H),2.54 (t, 2H).

EXAMPLE 12

Preparation of (S)-N-[[3-(3-fluoro-4-morpholinylphenyl)-2-oxo-5-oxazolidinyl]methyl]-4-(2-naphthyl)-4-oxobutanamide-N-oxide To a cooled solution (0-5° C.) of (S)-N-[[3-(3-fluoro-4-morpholinylphenyl)-2-oxo-5-oxazolidinyl]methyl]-4-(2-naphthyl)-4-oxobutanamide (0.950 gm, 0.0019 moles) in dichloromethane (150 ml) was added 60% m-CPBA (0.550 g, 0.0032 moles) and the resulting solution stirred at room temperature for 12 hr. The solvent was evaporated under reduced pressure and the residue chromatographed over silica gel (100-200 mesh, 40 g). The column was eluted with ethyl acetate (200 ml), followed by a mixture of chloroform:methanol (4:1, 600 ml). Concentration the combined fractions gave the title N-oxide (0.891 g, 82%) as a white solid.

$^1$H NMR (CDCl$_3$, δ): 8.59(t,1H), 8.36(s,1H),7.7-7.9 (m,5H), 7.2-7.5 (m,2H),7.08 (dd,1H), 6.60(t,1H), 4.76(m, 1H), 4.61(bt,2H), 3.5-4.3 (m, 9H), 3.42 (dd, 2H), 2.83 (bdd, 2H), 2.61 (bt, 2H).

EXAMPLE 13

Preparation of (S)-N-[[3-(3-fluoro-4-morpholinylphenyl)-2-oxo-5-oxazolidinyl]methyl]-4-oxo-4-(2-thienyl)butanamide-N-oxide To a cooled solution (0-5° C.) of (S)-N-[[3-(3-fluoro-4-morpholinylphenyl)-2-oxo-5-oxazolidinyl]methyl]-4-oxo- 4-(2-thienyl)butanamide (0.850 gm, 0.0017 moles) in dichloromethane (120 ml) was added 60% m-CPBA (0.550 g, 0.0032 moles) and the resulting solution stirred at room temperature for 12 hr. The solvent was evaporated under reduced pressure and the residue chromatographed over silica gel (100-200 mesh, 40 g). The column was eluted with ethyl acetate (200 ml) followed by a mixture of chloroform:methanol (4:1, 600 ml). Concentration of the combined fractions gave the tile N-oxide (0.790 g, 90%) as a white solid.

$^1$H NMR (CDCl$_3$, δ): 8.63(t,1H), 7.77(dd,1H), 7.65 (d, 1H), 7.56 (d, 1H), 7.09 (dd, 1H),7.04 (dd,1H), 6.45(t,1H), 4.68(m,1H), 4.65(bt,2H), 4.22(dt,2H), 3.89(t,1H), 3.5-3.9 (m, 5H), 3.22 (dd, 2H), 3.00 (bd,2H), 2.54 (t, 2H).

EXAMPLE 14

Preparation of (S)-N-[[3-(3-fluoro-4-morpholinylphenyl)-2-oxo-5-oxazolidinyl]methyl]-4-(4-chlorophenyl)-4-oxobutanamide-N-oxide To a cooled solution (0-5° C.) of (S)-N-[[3-(3-fluoro-4-morpholinylphenyl)-2-oxo-5-oxazolidinyl]methyl]-4-(4-chlorophenyl)-4-oxobutanamide, (1.150 gm, 0.0023 moles) in dichloromethane (150 ml) was added 60% m-CPBA (0.725 gm, 0.0040 moles) and the resulting solution stirred at room temperature for 12 hr. The solvent was evaporated under reduced pressure and the residue chromatographed over silica gel (100-200 mesh, 40 g). The column was eluted with ethyl acetate (200 ml) followed by a mixture of chloroform:methanol (4:1, 600 ml). Concentration of the combined fractions gave the title N-oxide (0.950 g, 80%) as a white solid.

$^1$H NMR (CDCl$_3$, δ): 8.61(t,1H), 7.76(d,2H), 7.72 (dd, 1H), 7.34 (d, 2H), 7.10 (dd, 1H), 6.46(t,1H), 4.70(m,1H), 4.64(bt,2H), 4.16 (dt,2H), 3.94(t, 1H), 3.5-3.9 (m, 5H), 3.24 (dd, 2H), 2.97 (bd,2H), 2.55 (t, 2H).

EXAMPLE 15

Preparation of (S)-N-[[3-(3-fluoro-4-morpholinylphenyl)-2-oxo-5-oxazolidinyl]methyl]-4-[4-(2'-methyl-4-propylphenyl)-4-oxobutanamide-N-oxide To a cooled solution (0-5° C.) of (S)-N-[[3-(3-fluoro-4-morpholinylphenyl)-2-oxo-5-oxazolidinyl]methyl]-4-[4-(2'-methyl-4-propylphenyl)-4-oxobutanamide (1.05 gm, 0.0020 moles) in dichloromethane (150 ml) was added 60% m-CPBA (0.600 gm) and the resulting solution stirred at room temperature for 12 hr. The solvent was evaporated under reduced pressure and the residue chromatographed over silica gel (100-200 mesh, 40 g). The column was eluted with ethyl acetate (200 ml) followed by a mixture of chloroform:methanol (4:1, 600 ml). Concentration of the combined fractions gave the title N-oxide (0.891 gm, 82%) as a white solid.

$^1$H NMR (CDCl$_3$, δ): 8.62(t,1H), 7.77 (dd,1H), 7.75 (d, 2H), 7.14 (d, 2H), 7.12 (dd, 1H), 6.44(t,1H), 4.75(m,1H), 4.64(bt,2H), 4.20 (dt,2H), 3.95(t,1H), 3.91 (t, 1H) 3.5-3.9 (m, 4H), 3.26 (dd,2H), 2.99(bd,2H), 2.57 (t, 2H),2.44(d,2H), 0.83 (d,6H).

EXAMPLE 16

Preparation of (S)-N-[[3-(3-fluoro-4-morpholinylphenyl)-2-oxo-5-oxazolidinyl]methyl]-4-(4-methylphenyl)-4-thiooxobutanamide To a solution of (S)-n-of (S)-N-[[3-(3-fluoro-4-morpholinylphenyl)-2-oxo-5-oxazolidinyl]methyl]-4-(4-methylphenyl)-4-oxo-butanamide (0.10 gm, 0.00021 moles) in dry THF (5 ml) was added Lawessons Reagent (0.052 gm, 0.000128 moles) and the resulting solution heated under reflux for 8 hr. The reaction mixture was cooled to room temperature and to this was added saturated aqueous sodium carbonate solution (3 ml) and then extracted with ethyl acetate. The solvent was evaporated off and the residue chromatographed over silica gel and eluted with a mixture of ethyl acetate-hexane to give the title compound (0.023 gm, 23%) as a white solid, mp 149-151° C.

$^1$H NMR (CDCl$_3$, δ): 8.60 (m, 1H), 7.68 (d, 2H), 7.34 (dd, 1H), 7.14 (d, 2H), 6.96 (dd, 1H), 6.81 (t, 1H), 4.90 (m, 1H), 4.20-4.40 (m, 1H), 3.80-4.0 (m, 4H), 3.50 (m, 2H), 2.90-3.00 (m, 6H).

EXAMPLE 17

Using the appropriate amine compound (II) and the carboxylic acid (III) and following exactly the method described in Examples 7-16 the following carboxylic acids can be prepared, viz.

(S)-N-[[3-(3-fluoro-4-morpholinylphenyl)-2-oxo-5-oxazolidinyl]methyl]-4-(4-methylphenyl)-4-oxobutanamide $^1$H NMR (CDCl$_3$, δ): 7.78 (d, 2H), 7.44 (d, 1H), 7.22 (d,2H), 7.09 (d, 1H), 6.88 (t, 1H), 6.41 (t, 1H), 4.76 (m, 1H), 3.6-4.1 (m, 4H), 3.86 (m, 4H), 3.31 (dd, 2H), 2.61 (t, 2H), 2.40 (s, 3H).

(S)-N-[[3-(3-fluoro-4-benzylpiperazinyl)phenyl]-2-oxo-5-oxazolidinyl]methy]-4-oxo-4-phenylbutanamide $^1$H-NMR (CDCl$_3$, δ): 7.88 (d,2H), 7.61 (dd, 1H), 7.38 (m, 5H), 7.2-7.4 (m, 5H), 6.88 (t, 1H), 6.55 (t, 1H), 4.77 (m, 1H), 3.94 (t, 1H), 3.5-3.7 (m, 3H), 3.71 (s, 2H), 3.34 (dd, 2H), 3.12 (m, 4H),3.12 (m, 4H), 2.61 (t, 2H).

(S)-N-[[3-(3-fluoro-4-[methylbenzylamin]phenyl)-2-oxo-5-oxazolidiny]methy]-4-(4-methyl phenyl)-4-oxobutanamide $^1$H NMR (CDCl$_3$, δ): 7.90 (d, 2H), 7.52 (dd, 1H), 7.2-7.5 (m, 8H), 7.05 (d, 1H), 6.84 (t, 1H), 6.50 (t, 1H), 4.75 (m, 1H), 4.48 (s, 2H), 3.95 (t, 1H), 3.6-4.1(m,3H), 3.64 (dd, 2H), 2.71 (s, 3H), 2.62 (t, 2H).

(S)-N-[[3-(3-fluoro-4-benzotriazolylpheny)-2-oxo-5-oxazolidinyl]methy]-4-oxo-4-phenylbutanamide $^1$H NMR (CDCl$_3$, δ): 8.16 (d, 1H), 7.84 (d, 2H), 7.66 (t, 1H), 7.2-7.6 (m, 8H), 6.46 (t, 1H), 4.90 (m, 1H), 3.98 (t,1H), 3.9-4.0 (m, 2H), 3.65 (m, 1H), 3.39 (ddd, 2H), 2.65 (ddd, 2H).

(S)-N-[[3-(3-fluoro-4-pyrrolidinylphen)-2-oxo-5-oxazolidinyl]methyl]-4-oxo-4-phenylbutanamide $^1$H NMR (CDCl$_3$, δ): 7.90 (d,2H), 7.52 (dd, 1H), 7.44 (d, 2H), (dd, 1H), 7.04 (dd, 1H), 6.65 (t, 1H), 6.43 (t, 1H), 4.74 (m,1 h), 3.93 (t, 1H), 3.77 (t, 1H), 3.6-3.8 (m, 2H), 3.33 (m, 6H), 2.63 (t, 3H), 1.94 (m, 4H).

(S)-N-[[3-(3-fluoro-4-benzotriazolylphenyl)-2-oxo-5-oxazolidinyl]methyl]-4-(4-methlyphenyl)-4-oxobutanamide ¹H NMR (CDCl₃, δ): 8.16 (d, 1H), 7.3-7.9(m,7H), 7.78 (d,2H), 7.21(d,1H), 6.54(t, 1H), 4.89 (m, 1H), 3.8-4.2 (m, 3H), 3.4-3.7 (m, 3H), 2.63 (dd, 2H), 2.23 (s, 3H).

(S)-N-[[3-(3-fluoro-4-thiomorpholinylphenyl)-2-oxo-5-oxazolidinyl]methyl]-4-oxo-4-phenylbutanamide ¹H NMR (CDCl₃, δ): 7.89 (d, 2H), 7.39-7.60 (m, 4H), 7.11 (dd, 1H), 6.90 (t, 1H), 6.39 (t, 1H), 4.76 (m, 1H), 3.94 (t, 1H), 3.80 (t, 1H), 3.6-3.7 (m, 2H), 3.36 (dd, 2H), 3.28 (m, 4H), 2.80 (m,4H), 2.62 (t, 2H).

(S)-N-[[3-(3-fluoro-4-benzylpiperazinyl)phenyl]-2-oxo-5-oxazolidinyl]methyl]-4-(4-methylphenyl)-4-oxobutanamide ¹H NMR (CDCl₃, δ): 7.81 (d, 2H), 7.2-7.5 (m, 8H), 7.08 (dd, 1H), 6.89 (t, 1H), 6.39 (t, 1H), 4.78 (m, 1H), 3.95(t, 1H), 3.79 (t, 1H), 3.6-3.7 (m, 2H), 3.61 (s, 2H), 3.31 (m, 2H), 3.09 (m,4H), 2.65 (m,6H), 2.41 (s, 3H).

(S)-N-[[3-(3-fluoro-4-piperidylphenyl)-2-oxo-5-oxazolidinyl]methyl]-4-oxo-4-phenylbutanamide ¹H NMR (CDCl₃, δ): 7.90(d,2H),7.60 (dd,1H),7.45(d,2H), 7.39 (dd,1H), 7.10 (dd,1H), 6.90 (t,1H), 6.55 (t,1H), 4.78(m, 1H), 3.95 (t, 1H), 3.80 (t, 1H), 3.4-3.7 (m, 2H), 3.35 (m, 2H), 3.00 (m,4H0,2.63 (t, 2H), 1.9-1.6 (m,6H).

(S)-N-[[3-(3-fluoro-4-piperidylphenyl)-2-oxo-5-oxazolidinyl]methyl]-4-(4-methylphenyl)-4-oxobutanamide ¹H NMR (CDCl₃, δ): 7.79(d,2H), 7.40 (dd,1H), 7.23(d, 2H), 7.09 (dd,1H), 6.91 (t,1H), 6.40 (t,1H), 4.77(m,1H), 3.98 (t, 1H), 3.80 (t, 1H), 3.4-3.7 (m, 2H), 3.30(t, 2H), 2.98 (m,4H), 2.62 (t, 2H), 2.41(s,3H), 1.6-1.9 (m,6H).

(S)-N-[[3-(3-fluoro-4-pyrrolidinylphenyl)-2-oxo-5-oxazolidinyl]methyl]-4-(4-methylphenyl)-4-oxobutanamide ¹H NMR (CDCl₃, δ): 7.80(d,2H),7.32 (dd,1H),7.21(d,2H), 7.01 (dd,1H), 6.60 (t,1H), 6.40 (t,1H), 4.75(m,1H),4.12(m 1H) 3.94 (t, 1H), 3.75 (t, 1H), 3.4-3.6 (m, 2H), 3.34 (m, 6H), 2.61 (t, 2H),2.40(s,3H), 1.9 (m,4H).

(S)-N-[[3-(3-fluoro-4-morpholinylphenyl)-2-oxo-5-oxazolidinyl]methyl]-4-(4-methoxyphenyl)-4-oxobutanamide ¹H NMR (CDCl₃, δ): 7.79(d,2H), 7.36 (dd,1H), 7.00 (dd, 1H), 6.82 (d,2H), 6.80(t,1H), 6.38 (t,1H), 4.69(m,1H), 3.80 (s, 3H), 3.78 (m, 4H), 3.4-4.0 (m, 4H), 3.20 (dt, 2H), 2.97 (m,4H),2.55 (dt, 2H).

(S)-N-[[3-(3-fluoro-4-morpholinylphenyl)-2-oxo-5-oxazolidinyl]methyl]-4-(2-naphthyl)-4-oxobutanamide ¹H NMR (CDCl₃, δ): 8.35 (s,1H),7.83(m, 4H), 7.50(m, 2H), 7.38 (dd, 1H), 7.01(dd,1H), 6.74 (t,1H), 6.41 (t,1H), 4.71(m,1H), 3.88 (t, 1H), 3.77 (m, 4H), 3.5-3.8 (m, 3H), 3.40 (dd, 2H), 2.91 (m,4H), 2.60(t, 2H).

((S)-N-[[3-(3-fluoro-4-morpholinylphenyl)-2-oxo-5-oxazolidinyl]methyl]-4-(2,4-difluorophenyl)-4-oxobutanamide ¹H NMR (CDCl₃, δ): 7.73(ddd,2H), 7.47 (dd,1H), 7.01(dd, 1H),6.7-6.9(m,3H), 6.30 (t,1H), 4.75(m,1H), 3.89 (m, 4H), 3.5-3.9 (m, 4H), 3.20 (m, 2H), 3.09(m,4H), 2.52 (t, 2H).

(S)-N-[[3-(3-fluoro-4-morpholinylphenyl)-2-oxo-5-oxazolidinyl]methyl]-4-[4-(2',2'-dimethyl-4-ethylphenyl)-4-oxobutanamide ¹H NMR (CDCl₃, δ): 7.75(d,2H), 7.37 (d,2H), 7.35(dd, 1H), 7.05 (dd, 1H), 6.82(t,1H), 6.37 (t,1H), 4.71(m,1H), 3.5-3.9 (m, 4H), 3.80 (m, 4H), 3.25 (dt, 2H), 2.97 (m,4H),2.54 (t, 2H), 1.26(s,9H).

(S)-N-[[3-(3-fluoro-4-[methylbenzylamino]phenyl)-2-oxo-5-oxazolidinyl]methyl]-4-(4-methoxyphenyl)-4-oxobutanamide ¹H NMR (CDCl₃, δ): 7.76(d,2H), 7.37 (dd,1H), 7.16(m, 5H), 6.93 (dd,1H), 6.79(d,2H),6.74 (t,1H), 6.37 (t,1H), 4.66 (m,1H),4.14 (s,2H), 3.84(t,1H), 3.74 (s,3H), 3.4-3.8 (m, 3H), 3.18 (dd, 2H), 2.62(s,3H),2.51 (t, 2H).

(S)-N-[[3-(3-fluoro-4-[methylbenzylamino]phenyl)-2-oxo-5-oxazolidinyl]methyl]-4-(2',2'-dimethyl-4-ethylphenyl)-4-oxobutanamide ¹H NMR (CDCl₃, δ): 7.77(d,2H), 7.37 (dd +d,3H), 7.19-7.22 (m,3H), 6.98 (dd,1H), 6.77(t,1H), 6.31 (t,1H), 4.69(m, 1H), 4.17(s,2H), 3.89(t,1H),3.72 (dd,1H), 3.5-3.6 (m, 2H), 3.25 (dd, 2H), 2.64 (s,3H),2.55 (t, 2H), 1.25(s,9H).

(S)-N-[[3-(3-fluoro-4-[methylbenzylamino]phenyl)-2-oxo-5-oxazolidinyl]methyl]-4-(2,4-dimethylphenyl)-4-oxobutanamide ¹H NMR (CDCl₃, δ): 7.65 (d,1H), 7.46 (dd,1H), 7.32(m, 5H), 7.04(m,3H), 6.95(t,1H), 6.36 (t,1H), 4.78(m,1H), 4.27 (s,2H), 3.97(t,1H), 3.6-3.8 (m, 2H), 3.81 (t, 1H), 3.27 (dd, 2H), 2.77 (s,3H), 2.61 (t, 2H), 2.44(s,3H), 2.35 (s, 3H).

(S)-N-[[3-(3-fluoro-4-morpholinylphenyl)-2-oxo-5-oxazolidinyl]methyl]-4-(2,4-dimethylphenyl)-4-oxobutanamide ¹H NMR (CDCl₃, δ): 7.652(d,1H), 7.42 (dd,1H), 7.0-7.1 (m,3H), 6.86(t,1H), 6.38 (t,1H), 4.79(m,1H), 3.95(t,1H), 3.5-3.9 (m,2H), 3.87 (m, 4H), 3.25(dd, 2H), 3.02 (m,4H), 2.59 (t, 2H), 2.41(s,3H), 2.34 (s, 3H).

(S)-N-[[3-(3-fluoro-4-pyrrolidinylphenyl)-2-oxo-5-oxazolidinyl]methyl]-4-(2,4-dimethylphenyl)-4-oxobutanamide ¹H NMR (CDCl₃, δ): 7.62(d,1H), 7.31 (dd, 1H), 7.03(s,+ dd, 3H), 6.60(t,1H), 6.36 (t,1H), 4.74(m,1H), 3.94(t,1H),3.76 (dd, 1H),3.67(m, 2H), 3.30 (m, 4H), 3.24 (dt, 2H), 2.60 (t, 2H), 2.44 (s,3H), 2.34 (s, 3H).1.94 (m,2H).

(S)-N-[[3-(3-fluoro-4-benztriazolylphenyl)-2-oxo-5-oxazolidinyl]methyl]-4-(2,4-dimethylphenyl)-4-oxobutanamide ¹H NMR (CDCl₃, δ): 8.15 (d,1H), 7.80 (dd,1H), 7.3-7.7 (m,6H), 7.02(d,2H), 6.39 (t,1H), 4.87(m,1H), 4.07(t,1H), 3.96(t,1H), 3.89 (dq, 1H), 3.75(dt,1H), 3.38 (qt, 2H), 2.62 (m, 2H), 2.39(s,3H), 2.26 (s, 3H).

(S)-N-[[3-(3-fluoro-4-pyrrolidinylphenyl)-2-oxo-5-oxazolidinyl]methyl]-4-oxo-4-(2-thienyl)butanamide ¹H NMR (CDCl₃, δ): 7.71 (d,1H), 7.63 (d,1H), 7.31 (dd, 1H), 7.11 (t, 1H),7.05(dd,1H), 6.68(m,1H), 6.38 (t,1H), 4.74 (m,1H), 3.95(t,1H), 3.77 (t, 1H), 3.6-3.7 (m, 2H), 3.36 (m, 4H), 3.28 (t, 2H), 2.63 (t, 2H), 1.96 (m,2H).

(S)-N-[[3-(3-fluoro-4-benztriazolylphenyl)-2-oxo-5-oxazolidinyl]methyl]-4-oxo-4-(2-thienyl)butanamide ¹H NMR (CDCl₃, δ): 8.08(d,1H), 7.77(dd,1H), 7.3-7.7(m, 7H), 7.02(t,1H), 6.45 (t,1H), 4.81(m,1H), 4.00(t,1H), 3.7-4.0 (m, 2H), 3.57 (dt, 1H), 3.25 (m, 2H), 2.55 (m,2H).

(S)-N-[[3-(3-fluoro-4-morpholinylphenyl)-2-oxo-5-oxazolidinyl]methyl]-4-oxo-4-phenylbut-2-enamide ¹H NMR (CDCl₃, δ): 7.92 (d,1H), 7.84 (d,1H), 7.2-7.6 (m, 6H), 6.98-7.1 (m, 3H), 4.38(m, 1H), 3.5-4.1 (m, 4H), 3.84 (m, 4H), 3.03 (m, 4H).

(S)-N-[[3-(3-fluoro-4-piperidylphenyl)-2-oxo-5-oxazolidinyl]methyl]-4-(4-methoxyphenyl)-4-oxobutanamide ¹H NMR (DMSOd₆, δ): 8.25 (t, 1H), 7.79 (d, 2H), 7.38 (dd, 1H), 7.71 (dd, 1H), 6.95 (t,1H), 6.93 (d, 2H+1H), 4.65 (m, 1H), 3.75 (s,3H), 3.99 (t, 1H), 3.64 (dd, 1H), 3.06 (t, 2H), 2.81(m,4H), 1.3-1.6 (m. 6H).

(S)-N-[[3-(3-fluoro-4-piperidylphenyl)-2-oxo-5-oxazolidinyl]methyl]-4-(4-chlorophenyl)-4-oxobutanamide ¹H NMR (CDCl₃, δ): 7.73(d,2H), 7.33 (d,2H), 7.2-7.8 (m, 2H), 6.96(dd,1H), 6.34 (t,1H), 4.72(m,1H), 3.84(t,1H), 3.5-3.8 (m, 3H), 3.21 (dd, 2H), 2.98 (m, 4H),2.54(t,2H), 1.5-1.7 (m,6H).

(S)-N-[[3-(3-fluoro-4-piperidylphenyl)-2-oxo-5-oxazolidinyl]methyl]-4-(2,4-dimethylphenyl)-4-oxobutanamide ¹H NMR (CDCl₃, δ): 7.55(d,2H), 7.4 (m,1H), 6.9-7.0 (m, 3H),6.32(t,1H), 4.70 (m,1H), 3.90(t,1H), 3.74 (t,1H), 3.5-3.7 (m, 2H), 3.20 (dd, 2H), 2.9-3.1 (m, 4H),2.52(t,2H), 2.34 (s,3H),2.71 (s, 3H), 1.5-1.9 (m,6H).

(S)-N-[[3-(3-fluoro-4-benztriazolylphenyl)-2-oxo-5-oxazolidinyl]methyl]-4-(4-methoxyphenyl)-4-oxobutanamide ¹H NMR (CDCl₃, δ): 8.07(d, 1H), 7.2-7.8 (m,6H), 7.71 (d,2H), 6.79 (d,2H), 6.51(t,1H), 4.81(m,1H), 3.4-4.0 (m, 4H), 3.71 (s, 3H), 3.15 (qt, 2H), 2.52 (dd, 2H).

(S)-N-[[3-(3-fluoro-4-benztriazolylphenyl)-2-oxo-5-oxazolidinyl]methyl]-4-(4-chlorophenyl)-4-oxobutanamide ¹H NMR (CDCl₃, δ): 8.09(d, 1H), 7.2-7.8 (m,6H), 7.75(d, 2H), 7.35 (d,2H), 6.29(t,1H), 4.81(m,1H), 3.7-4.0(m, 3H), 3.5-3.7 (bt, 1H),3.25 (qt, 2H), 2.55 (t, 2H).

(S)-N-[[3-(3-fluoro-4-(1,2,4-triazolyl)phenyl)-2-oxo-5-oxazolidinyl]methyl]-4-oxo-4-phenylbutanamide ¹H NMR (CDCl₃, δ): 8.62 (bs, 1H), 8.10 (s, 1H), 7.7-7.8 (m, 2H), 7.67 (dd, 2H,), 7.44 (t, 1H), 7.2-7.4 (m,3H), 6.49 (t, 1H), 4.78 (m, 1H), 3.8-4.0 (m, 3H), 3.55 (dt, 1H), 3.30 (ddd, 2H), 2.54 (dd, 2H).

(S)-N-[[3-(3-fluoro-4-(1,2,4-triazolyl)phenyl)-2-oxo-5-oxazolidinyl]methyl]-4-(4-methylphenyl)-4-oxobutanamide ¹H NMR (CDCl₃, δ): 8.71 (bs, 1H), 8.10 (s, 1H), 7.7-7.9 (m, 4H), 7.30 (d, 1H,), 7.21 (d, 2H), 6.63 (t, 1H), 4.86 (m, 1H), 3.8-4.1 (m, 3H), 3.64(dt, 1H), 3.35 (qdd, 2H), 2.5-2.6 (m, 2H), 2.35(s,3H).

(S)-N-[[3 (3-fluoro-4-(1,2,4-triazolyl)phenyl)-2-oxo-5-oxazolidinyl]methyl]-4-(4-methoxyphenyl)-4-oxobutanamide ¹H NMR (CDCl₃, δ): 8.68 (bs, 1H), 8.16 (s, 1H), 7.7-7.9 (m, 2H), 7.79(d, 2H) 7.28 (dd, 1H), 6.85 (d,2H), 6.58 (t, 1H), 4.86 (m, 1H), 3.8-4.1 (m, 3H), 3.82(s,3H), 3.61(dt, 1H), 3.32 (qdd, 2H), 2.65 (ddd, 2H).

(S)-N-[[3-(3-fluoro-4-(1,2,4-triazolyl)phenyl)-2-oxo-5-oxazolidinyl]methyl]-4-(2,4-dimethylphenyl)-4-oxobutanamide ¹H NMR (CDCl₃, δ): 8.69 (bs, 1H), 8.17 (s, 1H), 7.78 (t, 1H), 7.75 (d, 1H), 7.60 (d,1H),7.25 (d, 1H,), 7.10 (d, 1H),6.99 (s, 1H), 6.54(t, 1H), 4.86 (m, 1H), 3.8-4.1 (m, 3H), 3.65(dt, 1H), 3.25 (qt, 2H), 2.59 (dt, 2H), 2.38(s,3H), 2.29 (s,3H).

(S)-N-[[3-(3-fluoro-4-(1,2,4-triazolyl)phenyl)-2-oxo-5-oxazolidinyl]methyl]-4-oxo-4-(4-thiomethylphenyl)butanamide ¹H NMR (CDCl₃, δ): 8.57 (bs, 1H), 8.06 (s, 1H), 7.77 (m,2H), 7.61 (d, 2H), 7.19 (d, 1H), 7.10 (d, 2H), 6.47 (t, 1H), 4.76 (m, 1H), 3.8-4.0 (m, 3H), 3.55(dt, 1H), 3.25 (qdd, 2H), 2.55 (dq, 2H), 2.39 (s,3H).

(S)-N-[[3-(3-fluoro-4-(1,2,4-triazolyl)phenyl)-2-oxo-5-oxazolidinyl]methyl]-4-(2',2'-dimethyl-4-ethylphenyl)-4-oxobutanamide ¹H NMR (CDCl₃, δ): 8.58 (bs, 1H), 8.06 (s, 1H), 7.80(t, 1H), 7.6-7.8 (m, 1H), 7.67 (d, 2H,),7.32(d,2H), 7.26 (d, 1H), 6.43 (t, 1H), 4.77 (m, 1H), 3.7-4.0 (m, 3H), 3.55(dt, 1H), 3.25 (qt, 2H), 2.53(dt, 2H), 1.22(s,9H).

(S)-N-[[3-(3-fluoro-4-(1,2,4-triazolyl)phenyl)-2-oxo-5-oxazolidinyl]methyl]-4-(2'-methyl-4-propylphenyl)-4-oxobutanamide ¹H NMR (CDCl₃, δ): 8.61 (bs, 1H), 8.09 (s, 1H), 7.6-7.8 (m, 4H), 7.24 (dd, 1H,), 7.07 (d, 2H), 6.38 (t, 1H), 4.77 (m, 1H), 3.7-4.0 (m, 3H), 3.54(dt, 1H), 3.28(qt, 2H), 2.54(dt, 2H), 2.40(d,2H), 1.77 (pent.,1H), 0.81 (d,6H).

(S)-N-[[3-(3-fluoro-4-(1,2,4-triazolyl)phenyl)-2-oxo-5-oxazolidinyl]methyl]-4-oxo-4-(2-thienyl)butanamide ¹H NMR (CDCl₃, δ): 8.57 (bs, 1H), 8.05 (s, 1H), 7.76 (t,1H),7.60 (dd,1H), 7.53 (dd,1H), 7.25 (dd, 1H,), 7.01 (d, 2H), 6.47 (t, 1H), 4.78 (m, 1H), 3.7-4.0 (m, 3H), 3.56(ddd, 1H), 3.25 (qt, 2H), 2.54 (dt, 2H).

(S)-N-[[3-(3-fluoro-4-(1,2,4-triazolyl)phenyl)-2-oxo-5-oxazolidinyl]methyl]-4-(2-naphthyl)-4-oxobutanamide ¹H NMR (CDCl₃, δ): 8.41 (s, 1H), 8.27 (s, 1H), 8.02(s,1H), 7.3-7.9 (m,6H), 7.3-7.6 (m, 3H), 6.44 (t, 1H), 4.77 (m, 1H), 3.7-4.0 (m, 3H), 3.2-3.7 (m, 3H), 2.5-2.6 (m, 2H).

(S)-N-[[3-(3-fluoro-4-(1,2,4-triazolyl)phenyl)-2-oxo-5-oxazolidinyl]methyl]-4-(4-chlorophenyl)-4-oxobutanamide ¹H NMR (CDCl₃, δ): 8.58 (bs, 1H), 8.07 (s, 1H), 7.6-7.9 (m, 2H), 7.68 (d, 2H), 7.29 (d, 2H,), 7.2-7.3 (m, 1H), 6.31 (t, 1H), 4.81 (m, 1H), 3.7-4.1 (m, 3H), 3.55(dt, 1H), 3.25 (qt, 2H), 2.55(dt, 2H).

(S)-N-[[3-(3-fluoro-4-piperidylphenyl)-2-oxo-5-oxazolidinyl]methyl]-4-oxo-4-(2-thienyl)butanamide ¹H NMR (CDCl₃, δ): 7.5-7.7 (m, 2H), 7.3-7.5 (m,1H), 6.8-7.3 (m,3H), 6.35(t,1H), 4.69(m,1H), 3.89 (t,1H), 3.76(t,1H),3.59(m,2H), 3.21 (dd,2H),3.02 (m, 4H), 2.55 (t, 2H), 1.5-1.8 (m,6H).

(S)-N-[[3-(3-fluoro-4-piperidylphenyl)-2-oxo-5-oxazolidinyl]methyl]-4-(2'-methyl-4-propylphenyl)-4-oxobutanamide ¹H NMR (CDCl₃, δ): 8.08 (m, 1H), 7.74 (d, 2H), 7.4-7.8 (m, 1H), 7.16 (d, 2H,), 6.97(dd,1H) 6.37 (t, 1H), 4.74 (m, 1H), 3.88 (t, 1H), 3.80(t,1H), 3.4-3.71 (m, 2H), 3.40(m,4H) 3.25 (dd, 2H), 2.45(d, 2H), 1.80 (pent,1H), 1.5-1.8 (m,6H),0.83(d, 6H).

(S)-N-[[3-(3-fluoro-4-piperidylphenyl)-2-oxo-5-oxazolidinyl]methyl]-4-(4-acetamidophenyl)-4-oxobutanamide ¹H NMR (DMSOd₆,δ): 10.18 (s, 1H), 8.23(t, 1H), 7.78 (d, 2H), 7.60 (d, 2H), 7.36 (dd, 1H), 7.06 (dd, 1H), 6.93 (t,1H), 4.63 (m, 1H), 3.95(t,1H), 3.61 (dd,1H), 3.07(dd,1H), 2.81 (m,4H), 1.99 (s, 3H), 1.55 (m, 4H), 1.44 (m, 2H).

(S)-N-[[3-(3-fluoro-4-piperidylphenyl)-2-oxo-5-oxazolidinyl]methyl]-4-oxo-4-phenylbut-2-enamide ¹H NMR (CDCl₃, δ): 7.7-8.0 (m, 3H), 7.2-7.6 (m, 5H), 7.01 (d, 2H), 6.98 (t, 1H), 4.80 (m, 1H), 4.01 (t,1H), 3.85(t, 1H), 3.77 (t, 2H), 3.16 (m,4H), 1.5-1.9 (m, 6H).

(S)-N-[[3-(3-fluoro-4-pyrrolidinylphenyl)-2-oxo-5-oxazolidinyl]methyl]-4-oxo-4-(4-thiomethylphenyl)butanamide ¹H NMR (CDCl₃, δ): 7.70 (d,2H), 7.60 (bd,1H), 7.0-7.3 (m, 3H), 6.91 (d,1H), 6.47 (t, 1H), 4.71(m, 1H), 3.87(t,1H), 3.4-3.8 (m,3H), 3.45(m, 4H) 3.21 (dd, 2H), 2.54 (t, 2H), 2.45 (s,3H), 2.06(m,4H).

(S)-N-[[3-(3-fluoro-4-pyrrolidinylphenyl)-2-oxo-5-oxazolidinyl]methyl]-4-(2-naphthyl)-4-oxobutanamide ¹H NMR (CDCl₃, δ): 8.35 (s, 1H), 7.5-8.1 (m, 8H), 6.91 (d,1H) 6.53 (t, 1H), 4.72 (m, 1H), 3.38 (m, 4H), 3.2-4.0 (m, 6H), 2.61 (m, 2H), 1.99 (m,4H).

(S)-N-[[3-(3-fluoro-4-pyrrolidinylphenyl)-2-oxo-5-oxazolidinyl]methyl]-4-(2'-methyl-4-propylphenyl)-4-oxobutanamide ¹H NMR (CDCl₃, δ): 7.75 (d,2H), 7.46 (m,1H), 7.1-7.3 (m, 3H), 6.95 (d,1H), 6.44 (t, 1H), 4.70 (m, 1H), 3.3-4.0 (m,4H), 3.41 (m, 4H) 3.24 (dd, 2H), 2.55 (t, 2H), 2.45 (d,2H), 2.01 (m,4H), 1.81 (pent,1H), 0.83 (d, 6H).

(S)-N-[[3-(3-fluoro-4-pyrrolidinylphenyl)-2-oxo-5-oxazolidinyl]methyl]-4-(2',2'-dimethyl-4-ethylphenyl)-4-oxobutanamide ¹H NMR (CDCl₃, δ): 7.76 (d,2H), 7.2-7.5 (m, 4H), 6.95 (d,1H), 6.33 (t, 1H), 4.69(m, 1H), 3.88(t,1H), 3.71(t,1H), 3.6-3.7 (m,2H), 3.45(m, 4H) 3.23 (dd, 2H), 2.56 (t, 2H), 1.94 (m,4H), 1.26(s,9H).

(S)-N-[[3-(3-fluoro-4-pyrrolidinylphenyl)-2-oxo-5-oxazolidinyl]methyl]-4-(4-acetamidophenyl)-4-oxobutanamide ¹H NMR (CDCl₃, δ): 7.2-7.8 (m, 7H), 6.85 (d,1H), 6.47 (t, 1H), 4.67(m, 1H), 3.81(t,1H), 3.3-3.7 (m,3H), 3.46(m, 4H) 3.16 (m, 2H), 2.3-2.9 (m, 6H), 2.06 (s, 3H).

(S)-N-[[3-(3-fluoro-4-pyrrolidinylphenyl)-2-oxo-5-oxazolidinyl]methyl]-4-oxo-4-phenylbut-2-enamide ¹H NMR (CDCl₃, δ): 7.8-7.9 (m, 3H), 7.0-7.6 (m, 5H), 6.93 (d,1H), 6.75 (m,1H), 4.76 (m, 1H), 4.02(t,1H), 3.74 (m, 3H), 3.30 (m, 4H), 1.95 (m, 4H).

(S)-N-[[3-(3-fluoro-4-thiomorpholinylphenyl)-2-oxo-5-oxazolidinyl]methyl]-4-(4-methoxyphenyl)-4-oxobutanamide ¹H NMR (CDCl₃, δ): 7.78 (d,2H), 7.33 (dd,1H),6.99 (d,1H),6.83 (t,1H), 6.81 (d, 1H),6.38 (t, 1H) 4.69(m, 1H), 3.86 (t,1H), 3.79 (s,3H), 3.5-3.8 (m, 3H), 3.41 (m, 4H) 3.20 (m, 6H), 2.73(m,4H) 2.53 (t, 2H).

(S)-N-[[3-(3-fluoro-4-thiomorpholinylphenyl)-2-oxo-5-oxazolidinyl]methyl]-4-(2,4-dimethylphenyl)-4-oxobutanamide ¹H NMR (CDCl₃, δ): 7.55 (d,1H), 7.33 (dd,1H), 6.96 (m,3H), 6.81 (t,1H), 6.22 (t, 1H), 4.69(m, 1H), 3.88(t,1H), 3.5-3.8 (m,3H), 3.17(m, 6H) 2.73 (t, 2H), 2.45 (d,2H),2.51 (t,2H), 2.34(s,3H), 2.27 (s,3H).

(S)-N-[[3-(3-fluoro-4-thiomorpholinylphenyl)-2-oxo-5-oxazolidinyl]methyl]-4-oxo-4-(2-thienyl)butanamide ¹H NMR (CDCl₃, δ): 7.63 (d,1H), 7.55 (d,1H), 7.33 (dd, 1H), 7.05 (dd,2H), 6.85(t, 1H), 6.31 (t,1H), 4.69(m, 1H),3.88 (t,1H), 3.5-3.8 (m,3H), 3.23(m, 6H) 2.73 (m, 4H), 2.55 (t, 2H).

(S)-N-[[3-(3-fluoro-4-thiomorpholinylphenyl)-2-oxo-5-oxazolidinyl]methyl]-4-(4-acetamidophenyl)-4-oxobutanamide ¹H NMR (DMSOd₆, δ): 10.18 (s, 1H), 8.23(t, 1H), 7.73(d, 2H), 7.59 (d, 2H), 7.38 (dd, 1H), 7.08(dd,1H), 6.99 (t, 1H), 4.65 (m, 1H), 3.95(t,1H),3.62 (dd,1H), 3.08(m, 6H), 2.66 (m, 4H), 1.97 (s, 3H).

(S)-N-[[3-(3-fluoro-4-piperidylphenyl)-2-oxo-5-oxazolidinyl]methyl]-4-oxo-4-(4-thiomethylphenyl)butanamide ¹H NMR (CDCl₃, δ): 7.70 (d, 2H), 7.32 (dd,1H),7.14 (d, 2H,), 6.99(dd,1H), 6.82(t,1H), 6.33 (t, 1H), 4.68 (m, 1H), 3.86 (t, 1H), 3.4-3.8 (m, 3H), 3.20(dt, 2H), 2.90(t,4H) 2.53(t, 2H), 2.44(s,3H), 1.67 (m,4H), 1.5 (m,2H).

(S)-N-[[3-(3-fluoro-4-piperidylphenyl)-2-oxo-5-oxazolidinyl]methyl]-4-(naphthyl)-4-oxobutanamide ¹H-NMR (CDCl₃): 8.36 (s, 1H), 7.7-7.9 (m, 4H,), 7.4-7.6 (m, 2H), 7.32 (dd,1H), 6.99(d,1H), 6.78(t,1H), 6.43 (t, 1H), 4.70 (m, 1H), 3.87 (t, 1H), 3.5-3.8 (m, 3H), 3.39(dt,2H), 2.86(t,4H), 2.61(t, 2H), 2.10 (m,4H),1.50 (m,2H).

S)-N-[[3-(3-fluoro-4-piperidylphenyl)-2-oxo-5-oxazolidinyl]methyl]-4-(2',2'-dimethyl-4-ethylphenyl)-4-oxobutanamide ¹H NMR (CDCl₃, δ): 7.75 (d,2H), 7.37 (d,2H),7.31 (dd, 1H,), 7.00(dd,1H), 6.84(t,1H), 6.37 (t, 1H), 4.68 (m, 1H), 3.87 (t, 1H), 3.5-3.8 (m, 3H), 3.25 (dt, 2H), 2.91 (t,4H) 2.54(t, 2H), 2.23(m,4H), 1.5 (m,2H), 1.26(s,9H).

(S)-N-[[3-(3-fluoro-4-benztriazolylphenyl)-2-oxo-5-oxazolidinyl]methyl]-4-oxo-4-(4-thiomethylphenyl)butanamide ¹H NMR (CDCl₃, δ): 8.08 (d, 2H), 7.77 (dd, 1H,), 7.63(d, 2H), 7.2-7.5 (m, 4H), 7.12 (d,2H), 6.41 (t, 1H), 4.81 (m, 1H), 3.98 (t, 1H), 3.7-3.9 (m, 2H), 3.54(dt,1H), 3.22(qdd,2H), 2.54(dd, 2H), 2.36(s,3H).

(S)-N-[[3-(3-fluoro-4-benztriazolylphenyl)-2-oxo-5-oxazolidiny]methyl]-4-(2-naphthyl)-4-oxobutanamide ¹H NMR (CDCl₃, δ): 8.35(s,1H), 8.08 (d, 1H), 7.6-7.8(m, 5H), 7.2-7.6 (m, 7H), 6.41 (t, 1H), 4.82 (m, 1H), 3.8-4.0 (m, 3H), 3.3-3.7(m,3H), 2.64(dd, 2H).

(S)-N-[[3-(3-fluoro-4-benztriazolylphenyl)-2-oxo-5-oxazolidinyl]methyl]-4-(2',2'-dimethyl-4-ethylphenyl)-4-oxobutanamide ¹H NMR (CDCl₃, δ): 8.08 (d, 1H), 7.80 (dd, 1H,), 7.70(d, 2H), 7.57(t, 1H), 7.2-7.5 (m, 4H), 7.08 (d,2H), 6.41 (t, 1H), 4.80 (m, 1H), 3.7-4.0 (m, 3H), 3.55(dt,1H), 3.1-3.4(m,2H), 2.54(dd, 2H), 2.37(d,2H), 1.72(pent,1H), 0.76(d,6H).

(S)-N-[[3-(3-fluoro-4-benzotriazolylphenyl)-2-oxo-5-oxazolidinyl]methyl]-4-oxo-4-phenylbut-2-enamide ¹H NMR (CDCl₃, δ): 7.2-8.0 (m,13H), 6.95 (d,1H), 6.65 (m,1H), 4.89(m, 1H), 4.18(t,1H), 3.7-4.0 (m, 3H).

(S)-N-[[3-(3-fluoro-4-benztriazolylphenyl)-2-oxo-5-oxazolidinyl]methyl]-4-(4-acetamidophenyl)-4-oxobutanamide ¹H NMR (DMSOd₆, δ): 10.16 (s, 1H), 8.29(t, 1H), 8.12 (d, 1H), 7.79 (m, 4H), 7.58 (d, 2H), 7.4-7.5 (m, 4H), 4.74 (m, 1H), 4.13(t,1H),3.08(dd,1H), 3.10(t, 2H), 1.97 (s, 3H).

(S)-N-[[3-fluoro-4-thiomorpholinylphenyl)-2-oxo-5-oxazolidinyl]methyl]-4-(2',2'-dimethyl-4-ethylphenyl)-4-oxobutanamide ¹H NMR (CDCl₃, δ): 7.76 (d, 2H), 7.53 (dd, 1H),7.39 (d, 2H+1H), 7.02(d,1H), 6.29 (t, 1H), 4.71 (m, 1H), 3.89 (t, 1H), 3.79(t,1H), 3.5-3.7 (m, 2H), 3.38(m, 4H), 3.24 (dd,2H), 2.92 (m,4H) 2.54(t, 2H), 1.26(s,9H).

(S)-N-[[3-(3-fluoro-4-thiomorpholinylphenyl)-2-oxo-5-oxazolidinyl]methyl]-4-oxo-4-phenylbut-2-enamide ¹H NMR (CDCl₃, δ): 7.8-7.9 (m,3H), 7.3-7.7 (m, 5H), 6.8-7.0 (m,3H), 4.81(m,1H), 4.05(m,1H), 3.75 (m, 3H), 3.49 (m, 4H), 3.10 (m, 4H).

(S)-N-[[3-(3-fluoro-4-thiomorpholinylphenyl)-2-oxo-5-oxazolidinyl]methyl]-4-(β-naphthyl)-4-oxobutanamide ¹H NMR (CDCl₃, δ): 8.35 (s, 1H), 7.7-8.0 (m, 4H), 7.3-7.7 (m, 5H), 7.01 (m, 1H), 6.48 (m, 1H), 4.74 (m, 1H), 3.80 (m, 3H), 3.60 (m, 1H), 3.37 (m, 6H), 2.93 (m, 4H), 2.60 (m, 2H)

(S)-N-[[3-(3-fluoro-4-thiomorpholinylphenyl)-2-oxo-5-oxazolidinyl]methyl]-4-(4-chlorophenyl)-4-oxobutanamide ¹H NMR (CDCl₃, δ): 7.74 (d, 2H), 7.54 (d, 1H), 7.34 (d, 2H+1H), 6.98 (d, 1H), 6.35 (t, 1H), 4.78 (m, 1H), 3.88 (t, 1H), 3.5-3.8 (m, 3H), 3.38 (m, 4H), 3.22 (dd, 2H), 2.93 (m, 4H), 2.54 (t, 2H).

(S)-N-[[3-(3-fluoro-4-thiomorpholinylphenyl)-2-oxo-5-oxazolidinyl]methyl]-4-(2,4-dimethyl-4 ethylphenyl)-4-oxobutanamide ¹H NMR (CDCl₃, δ): 7.95 (m, 1H), 7.74 (d, 2H+1H), 7.77 (d, 2H), 7.07 (d, 1H), 6.38 (t, 1H), 4.76 (m, 1H), 3.91 (t,1H), 3.4-3.8 (m,3H), 3.58 (m,4H), 3.25 (dd, 2H), 3.1 (m, 4H), 2.54 (t, 2H), 2.46 (d, 2H), 1.80 (pent, 1H), 0.85 (s, 3H), 0.82 (s, 3H).

Microbiology:

Pharmacological Testing

The compound of formula (I) of the present invention displayed antimycobacterial activity when tested by in vitro growth inhibition assay and agar incorporation methods. The minimum inhibitory concentrations (μg/ml) obtained for representative compounds of formula (I) against *M. tuberculosis* including sensitive and resistant strains are summarized in Table-I. The MIC value of a representative preferred Compound No. 30 of formula I against different species of mycobacteria is summarized in Table-II.

In vitro Growth Inhibition Assay

The ability of the compounds 1-78 of formula (I) of this invention to inhibit the growth of *Mycobacterium* species was determined by the BACTEC 460 TB system. The reference strain *M. tuberculosis* H37Rv ATCC 27294 was grown in Middlebrook 7H9 broth containing 10% ADC supplement at 37° C. on a rotay shaker at 150 rpm for grown for 7 days. The turbidity of the culture was adjusted to 1.0 Mc farland. The BACTEC 7H12B medium vials were seeded with 0.1 ml of the 1.0 Mc farland adjusted *M. tuberculosis* culture. In the control vials 0.1 ml of the culture was added after 100 fold dilution of the initial inoculum. Stock solution of 1 mg/ml of each compound was prepared in DMSO in separate sterile tubes. The compounds were further diluted to concentration of 25 μg/100 μl, 0.1 ml was than added to the 7H12B vial containing mycobacterial culture so that final concentration of the compound 6.25 μg/ml. The cap in all the vials were cleaned with isopropanyl alcohol and kept in racks. The vials were then incubated at 37° C. without shaking. Test vials was read daily on the BACTEC system till the GI of the control vial reached >30. Once the GI in the control reached 30 ΔGI ($GI=GI_{(n)}-GI_{(n-1)}$) was determined for all test and control vials. If ΔGI of test vial is less than that of the control vial the culture was sensitive to the test compound.

In vitro Agar Dilution Assay

MIC of compound of formula (I) of this invention against strains of *mycobacterium* were determined by a reference agar dilution method as per the NCCLS-M24-T2. recommendations. The compounds were dissolved in DMSO and diluted twofold to obtain ten serial dilutions of each compound. Appropriate volume of compounds were incorporated into duplicate plates of Middlebrook 7H10 agar medium supplemented with 10% Middlebrook 7H10 supplement oleic acid-albumin-dextrose (OADC) enrichment at concentration of 0.03 μg/ml to 16 μg/ml. Test organisms (*mycobacterium* strains) were grown in Middle brook 7H9 broth containing 0.05% Tween-80 and 10% ADC supplement. After 7 days of incubation at 37° C. the broths were adjusted to the turbidity of 1.0 McFarland standard; the organism were further diluted 10 fold in sterile water containing 0.10% Tween-80. The resulting mycobacterial suspensions were spotted (3-5 μl/spot) onto drug supplemented 7H10 media plates. The plates were sealed and incubated at 37° C. for 3-4 weeks in upright position. The MIC was recorded as the lowest dilution of the drug that completely inhibited the growth of test organisms. Test isolates included 10 clinical isolates that were generally susceptible to common tubercular agents and 10 strains that were resistant to one or more standard anti tubercular drugs. Appropriate reference strains and control drug was included in each batch of test.

In vivo Studies:

The efficacy of the compound of formula (I) of this invention was also evaluated in murine model of pulmonary tuberculosis. *Mycobacterium tuberculosis* cultures grown in Middle brook 7H9 broth containing 0.05% Tween-80 and 10% ADC supplement at 37° C. for 7 days on a rotary shaker. For, animal inoculation liquid cultures were declumped by brief sonication and were diluted appropriately in 7H9 broth to obtain a concentration of $1\times10^7$ CFU's/0.2 ml. Four-week-old male outbred Swiss albino mice housed in a pathogen free, biosafety level 3 environment within micro isolator cages were used throughout the study. Infections were produced by intravenous inoculation into caudal tail vein of 0.2 ml of declumped *M. tuberculosis* suspension. Following infection, mice were randomly distributed in different groups of six each.

Treatment for initial study was started one day after infection. For, treatment Compound No. 30 of formula I was dissolved in 10% PEG. Isoniazid was dissolved in sterile water. The drugs were prepared each morning prior to administration. Therapy was given 5 days per week for four weeks. All the agents were administered by gavage and were dosed at 50, 25, 12.5 mg/kg of body weight. Control group of infected but untreated mice were killed at the initiation of therapy (early control) or at the end of the treatment period (late control). Mice were sacrificed by cervical dislocation 3-5 days after the administration of the last dose of drug. The spleens and right lung were removed aseptically and homogenized in tissue homogeniser. At least 4 serial tenfold dilution of the homogenate was plated onto selective Middlebrook 7H11 agar plates in duplicate. The colony counts were recorded after incubation at 37° C. for 4 weeks. The viable cell counts were converted to $Log_{10}$ values. A compound showing 2 Log reduction in viable counts compared to the controls was considered significant.

The in vivo data for a representative compound of formula (I) is given in Table-II.

Acute toxicity of Compound No. 30 of Chart-I was estimated in mice and the $LD_0$ was found to be >1000 mg/kg P. O.

TABLE I in vitro activity of compounds 1 to 58 of formula (I),

| Compound No. | Growth inhibition of M. tuberculosis 27294 | MIC (μg/ml) against M. tuberculosis 27294 | Clinical isolates Sensitive | Resistant |
|---|---|---|---|---|
| 1 | + | 16 | 4-16 | >16 |
| 2 | + | 8 | 8 | 8 |
| 8 | + | 2 | .5-2 | 2-4 |
| 13 | + | 2 | 2 | 2-4 |
| 14 | + | 0.25 | 0.25-0.5 | 4->16 |
| 15 | + | >16 | >16 | >16 |
| 16 | + | 0.5 | 0.5 | 0.5(>16) |
| 17 | + | 0.5 | 1.0 | 0.5-1.0 |
| 18 | + | 4- | 1-4 | 8->16 |
| 19 | + | 2 | 1-2 | 2 |
| 20 | + | 1 | 1-2 | 2-4 |
| 21 | + | 0.5 | 0.5-2 | 0.5(>16) |
| 25 | + | 4 | 4-16 | 4->16 |
| 27 | + | >16 | >16 | >16 |
| 28 | + | 0.5 | 1-2 | 2-8 |
| 30 | + | 0.5 | 0.5 | 0.5-2 |
| 31 | + | 1 | 1-2 | 1-4 |
| 32 | + | 0.25 | 0.25-0.5 | 4-(>16) |
| 33 | + | 0.5 | 1 | 0.5-2 |
| 34 | + | >16 | >16 | >16 |
| 35 | + | 4 | 2-4 | 4-8 |
| 36 | + | 4 | 4-8 | 4-8 |
| 39 | + | 2 | 2-4 | 2-8 |
| 40 | + | 1 | 1-2 | 1-2 |
| 43 | + | 1 | 0.5-1.0 | 1-2 |
| 44 | + | 1 | 0.5-2 | 1-4 |
| 45 | + | 2.0 | 2-4 | 2-4 |
| 46 | + | 2 | 2-4 | 2-8 |
| 47 | + | 1 | 1-2 | 2-4 |
| 48 | + | 2 | 2-4 | 2-8 |
| 49 | + | 4 | 4-16 | 4-16 |
| 50 | + | 2 | 2-4 | 2-4 |
| 51 | + | 8 | 8->16 | 8->16 |
| 52 | + | 2 | 2 | 4->16 |
| 53 | + | >16 | >16 | >16 |
| 54 | + | 8 | 8-16 | >16 |
| 55 | + | >16 | >16 | >16 |
| 56 | + | >16 | >16 | >16 |

TABLE I-continued in vitro activity of compounds 1 to 58 of formula (I).

| Compound No. | Growth inhibition of M. tuberculosis 27294 | MIC (μg/ml) against | | |
|---|---|---|---|---|
| | | M. tuberculosis 27294 | Clinical isolates | |
| | | | Sensitive | Resistant |
| 57 | + | 16 | 16->16 | >16 |
| 58 | + | 8 | 8->16 | 8->16 |
| Isoniazid | + | 0.25 | 0.12-.25 | 8->16 |
| Linezolid | + | 0.5 | 0.25-0.5 | 1.0-2.0 |

TABLE II

MIC values of compound of formula (I) against different species of Mycobacteria

| | | MIC (μg/ml) | | | | |
|---|---|---|---|---|---|---|
| Sr. No. | Compound No. | M. tuberculosis | | M. avium-intracellular complex | M. fortuitum | M. kansai |
| | | Sensitive | Resistant | | | |
| 1 | Compound 30 of formula I | 0.50 | 0.50-2.0 | 8.0->16.0 | >16.0 | 8.0 |
| 2 | Isoniazid | 0.25 | 4.0->16.0 | 8.0->16.0 | >16.0 | >16.0 |

TABLE III in vivo activity of Compound of formula (I) against M. tuberculosis ATCC 27294[a] infection in Swiss albino mice

| Sr. No. | Drug & Dose[b] (mg/kg day$^{-1}$) or group | Mean Log$_{10}$ No. of CFU | | Mean Log$_{10}$ No. of reduction[c] | |
|---|---|---|---|---|---|
| | | Lung | Spleen | Lung | Spleen |
| 1 | Compound 30 of Chart-I | | | | |
| | 50 mg/kg | 2.12 | 2.09 | 2.40 | 2.53 |
| | 25 mg/kg | 2.21 | 2.13 | 2.30 | 2.49 |
| | 12.5 mg/kg | 4.34 | 4.30 | 0.20 | 0.26 |
| 2 | Isoniazid | | | | |
| | 50 mg/kg | 2.03 | 1.92 | 2.49 | 2.70 |
| | 25 mg/kg | 2.11 | 2.11 | 2.41 | 2.51 |
| | 12.5 mg/kg | 2.95 | 2.94 | 1.57 | 1.68 |
| 3 | Infected early control | 4.52 | 4.62 | | |
| 4 | Infected late control | 6.57 | 6.37 | | |

[a]inoculation of log$_{10}$:- 7.00 Mycobacteria.
[b]mice were dosed 5 day/week for 4 weeks. From day 1-28.
[c]difference in mean log$_{10}$ number CFU from that of early controls.

The compound of formula I of this invention may be administrated to a subject such as a human being or an animal in need of such an administration through any route appropriate to the condition to be treatede. Suitable routes of administration include oral, rectal, nasal, topical (both buccal and sublingual), vaginal and parenteral (including subcutaneous, intramuscular, intradermal, intrathecal and epidural).

Pharmaceutical compositions of compound of formula I can be prepared in adjunction with inert pharmaceutically acceptable carriers, which can either be solid or liquid.

Solid form preparations include powders, tablets, dispersible granules, capsules, cachets, suppositories and ointments. The solid carriers can be one or more substances which may act also as diluents, flavouring agents, solubilisers, lubricants, suspending agents, binders or tablet disintegrating agents. It can also be finely divided solid which is in admixture with finely divided active compound. Suitable solid carriers are lactose, pectin, dicalcium phosphate, microcrystalline cellulose, sucrose, kaolin, dextrin, gelatin, starch, tragacanth, low melting wax, coca butter and the like.

Liquid preparations include solutions, suspensions and emulsions, e.g. solutions of compound of formula I in water or water-propylene glycol mixture for parenteral injection. Liquid preparations can also be formulated along with non-ionic surfactants and edible oils such as corn, peanut and sesame oils. Aqueous solutions for oral use can be prepared by dissolving the active component in water and adding suitable colorants, flavours stabilizing and thickening agents, as required. Aqueous suspension for oral use can be made by dispersing the finely divided active component in water with a viscous material, e.g. natural or synthetic gums, resins, methyl cellulose, sodium carboxymethyl cellulose and the known suspending agents. The adjuvants may also include preserving agents and anti-oxidants.

Compositions for topical application may take the form of liquids or gels, containing a therapeutically effective concentration of compound of formula I admixed with a dermatologically acceptable carrier.

The pharmaceutical preparations may be in unit dosage form. In such form, the preparation is subdivided into unit doses containing appropriate quantities of the active component. The unit dosage can be in the form of tablets, capsules, powders in vials or ampoules, ointments, gels, creams or any other form. The quantity or concentration of the active compound in such unit dose preparations may be varied or adjusted according to the particular application and potency of the active ingredient.

What is claimed is:

1. A compound of formula (I) and its pharmaceutically acceptable salts

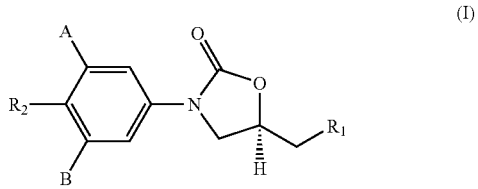

(I)

wherein,

A is either hydrogen or fluorine,

B is either hydrogen or fluorine, wherein one of A and B is hydrogen and the other is fluorine, R₁ is a group of formula,

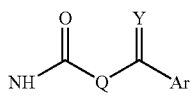

wherein,

Q is either an alkyl group of two carbon atoms, an alkene group of two carbon atoms or an alkyne group of two carbon atoms Y is oxygen;

Ar is a substituted phenyl ring or a substituted pyridine ring of formula

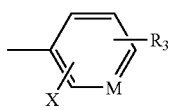

or Ar is a five membered ring of formula

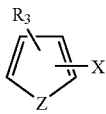

or Ar is a fused bicyclic phenyl or pyridine ring of formula

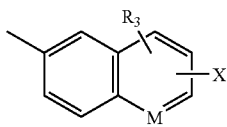

wherein,

M is either CH or N

Z is CH, NH, O, or S,

X is a group selected from $OR_4$, $NR_4R_5$, $NO_2$, $SR_4$, $SOOR_4$, $SOONR_4R_5$, F, Cl, Br or I, wherein $R_4$ is as defined hereinbefore, and $R_3$ is an alkyl group of 1-4 carbon atoms, both saturated and unsaturated, which can be straight or branched; cycloalkyl of 3-7 carbon atoms; CHO, —COOH, —COOR₄; —COCR₄; CN; aryl or heteroaryl;

wherein, $R_4$ is an alkyl group of 1-4 carbon atoms, an alkene of 3-6 carbon atoms, an alkyne of 3-6 carbon atoms;

$R_5$ is hydrogen or $R_4$ $R_2$ is selected from the groups shown below, and the corresponding N-oxides thereof;

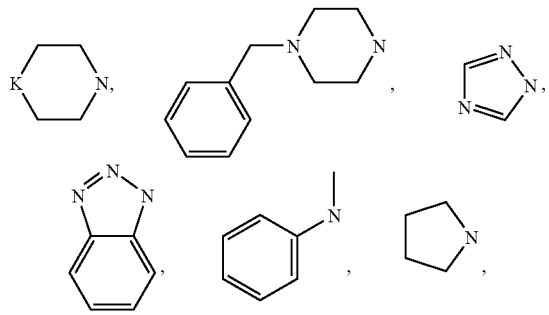

Heteroaryl or Heterocycloalkyl wherein K is O, S, SO, $SO_2$, or $CH_2$.

2. A compound according to claim 1, wherein in said compound of formula I Aryl in the definition of R3 is phenyl substituted with (0) or (1) of ⁻F, ⁻Cl, ⁻OCH₃, ⁻OH, ⁻NH₂, ⁻C₁-C₄ alkyl, ⁻O—C(O)—OCH₃, ⁻NO₂ or ⁻CN.

3. A compound according to claim 1, wherein said compound of formula I is selected from the group consisting of:
1) (S)-N-[[3-(3-fluoro-4-morpholinylphenyl)-2-oxo-5-oxazolidinyl]methyl]-4-oxo-4-phenylbutanamide;
2) (S)-N-[[3-(3-fluoro-4-morpholinylphenyl)-2-oxo-5-oxazolidinyl]methyl]-4-(4-methylphenyl)-4-oxobutanamide;
3) (S)-N-[[3-(3-fluoro-4-benzylpiperazinyl)phenyl]-2-oxo-5-oxazolidinyl]methyl]-4-oxo-4-phenylbutanamide;
4) (S)-N-[[3-(3-fluoro-4-[methylbenzylamino]phenyl)-2-oxo-5-oxazolidinyl]methyl]-4-(4-methyl phenyl)-4-oxobutanamide;
5) (S)-N-[[3-(3-fluoro-4-benzotriazolylphenyl)-2-oxo-5-oxazolidinyl]methyl]-4-oxo-4-phenylbutanamide;
6) (S)-N-[[3-(3-fluoro-4-pyrrolidinylphenyl)-2-oxo-5-oxazolidinyl]methyl]-4-oxo-4-phenylbutanamide;
7) (S)-N-[[3-(3-fluoro-4-benzotriazolylphenyl)-2-oxo-5-oxazolidinyl]methyl]-4-(4-methlyphenyl)-4-oxobutanamide;
8) (S)-N-[[3-(3-fluoro-4-thiomorpholinylphenyl)-2-oxo-5-oxazolidinyl]methyl]-4-oxo-4-phenylbutanamide;
9) (S)-N-[[3-(3-fluoro-4-benzylpiperazinyl)phenyl]-2-oxo-5-oxazolidinyl]methyl]-4-(4-methlyphenyl)-4-oxobutanamide;
10) (S)-N-[[3-(3-fluoro-4-piperidylphenyl)-2-oxo-5-oxazolidinyl]methyl]-4-oxo-4-phenylbutanamide;
11) (S)-N-[[3-(3-fluoro-4-piperidylphenyl)-2-oxo-5-oxazolidinyl]methyl]-4-(4-methlyphenyl)-4-oxobutanamide;
12) (S)-N-[[3-(3-fluoro-4-pyrrolidinylphenyl)-2-oxo-5-oxazolidinyl]methyl]-4-(4-methlyphenyl)-4-oxobutanamide;
13) (S)-N[[3-(3-fluoro-4-morpholinylphenyl)-2-oxo-5-oxazolidinyl]methyl]-4-(4-methoxyphenyl)-4-oxobutanamide;
14) (S)-N-[[3-(3-fluoro-4-morpholinylphenyl)-2-oxo-5-oxazolidinyl]methyl]-4-(4-chlorophenyl)-4-oxobutanamide;
16) (S)-N-[[3-(3-fluoro-4-morpholinylphenyl)-2-oxo-5-oxazolidinyl]methyl]-4-(4-2-naphthyl)-4-oxobutanamide;
17) (S)-N-[[3-(3-fluoro-4-morpholinylphenyl)-2-oxo-5-oxazolidinyl]methyl]-4-[4-(2'-methyl-4-propylphenyl)-4-oxobutanamide;

18) (S)-N-[[3-(3-fluoro-4-morpholinylphenyl)-2-oxo-5-oxazolidinyl]methyl]-4-(2,4-difluorophenyl)-4-oxobutanamide;
19) (S)-N-[[3-(3-fluoro-4-morpholinylphenyl)-2-oxo-5-oxazolidinyl]methyl]-4-oxo-4-(2-thienyl)butanamide;
20) (S)-N-[[3-(3-fluoro-4-morpholinylphenyl)-2-oxo-5-oxazolidinyl]methyl]-4[-4-(2',2'-dimethyl-4-ethylphenyl)-4-oxobutanamide;
21) (S)-N-[[3-(3-fluoro-4-morpholinylphenyl)-2-oxo-5-oxazolidinyl]methyl]-4-oxo-4-(4-thiomethyl)phenylbutanamide;
22) (S)-N-[[3-(3-fluoro-4-[methylbenzylamino]phenyl)-2-oxo-5-oxazolidinyl]methyl]-4-(4-methoxyphenyl)-4-oxobutanamide;
23) (S)-N-[[3-(3-fluoro-4-[methylbenzylamino]phenyl)-2-oxo-5-oxazolidinyl]methyl]-4-(2',2'-dimethyl-4-ethylphenyl)-4-oxobutanamide;
24) (S)-N-[[3-(3-fluoro-4-[methylbenzylamino]phenyl)-2-oxo-5-oxazolidinyl]methyl]-4-(2,4-dimethylphenyl)-4-oxobutanamide;
25) (S)-N-[[3-(3-fluoro-4-morpholinylphenyl)-2-oxo-5-oxazolidinyl]methyl]-4-(2,4-dimethylphenyl)-4-oxobutanamide;
26) (S)-N-[[3-(3-fluoro-4-pyrrolidinylphenyl)-2-oxo-5-oxazolidinyl]methyl]-4-(2,4-dimethylphenyl)-4-oxobutanamide;
27) (S)-N[[3-(3-fluoro-4-benzotriazolylphenyl)-2-oxo-5-oxazolidinyl]methyl]-4-(2,4-dimethylphenyl)-4-oxobutanamide;
28) (S)-N-[[3-(3-fluoro-4-pyrrolidinylphenyl)-2-oxo-5-oxazolidinyl]methyl]-4-oxo-4-(2-thienyl)butanamide;
29) (S)-N-[[3-(3-fluoro-4-benzotriazolylphenyl)-2-oxo-5-oxazolidinyl]methyl]-4-oxo-4-(2-thienyl)butanamide;
30) (S)-N-[[3-(3-fluoro-4-morpholinylphenyl)-2-oxo-5-oxazolidinyl]methyl]-4-(4-2-naphthyl)-4-oxobutanamide-N-oxide;
31) (S)-N-[[3-(3-fluoro-4-morpholinylphenyl)-2-oxo-5-oxazolidinyl]methyl]-4-oxo-4-(2-thienyl)butanamide-N-oxide;
32) (S)-N-[[3-(3-fluoro-4-morpholinylphenyl)-2-oxo-5-oxazolidinyl]methyl]-4-(4-chlorophenyl)-4-oxobutanamide-N-oxide;
33) (S)-N-[[3-(3-fluoro-4-morpholinylphenyl)-2-oxo-5-oxazolidinyl]methyl]-4-[4-(2'-methyl-4-propylphenyl)-4-oxobutanamide-N-oxide;
34) (S)-N-[[3-(3-fluoro-4-morpholinylphenyl)-2-oxo-5-oxazolidinyl]methyl]-4-oxo-4-phenylbut-2-enamide;
35) (S)-N-[[3-(3-fluoro-4-piperidylphenyl)-2-oxo-5-oxazolidinyl]methyl]-4-(4-methoxyphenyl)-4-oxobutanamide;
36) (S)-N-[[3-(3-fluoro-4-piperidylphenyl)-2-oxo-5-oxazolidinyl]methyl]-4-(4-chlorophenyl)-4-oxobutanamide;
37) (S)-N-[[3-(3-fluoro-4-piperidylphenyl)-2-oxo-5-oxazolidinyl]methyl]-4-(2,4-dimethylphenyl)-4-oxobutanamide;
38) (S)-N-[[3-(3-fluoro-4-benztriazolylphenyl)-2-oxo-5-oxazolidinyl]methyl]-4-(4-methoxyphenyl)-4-oxobutanamide;
39) (S)-N-[[3-(3-fluoro-4-benzotriazolylphenyl)-2-oxo-5-oxazolidinyl]methyl]-4-(4-chlorophenyl)-4-oxobutanamide;
40) (S)-N-[[3-(3-fluoro-4-(1,2,4-triazolyl)phenyl)-2-oxo-5-oxazolidinyl]methyl]-4-oxo-4-phenylbutanamide;
41) (S)-N-[[3-(3-fluoro-4-(1,2,4-triazolyl)phenyl)-2-oxo-5-oxazolidinyl]methyl]-4-(4-methylphenyl)-4-oxobutanamide;
42) (S)-N-[[3-(3-fluoro-4-(1,2,4-triazolyl)phenyl)-2-oxo-5-oxazolidinyl]methyl]-4-(4-methoxyphenyl)-4-oxobutanamide;
43) (S)-N-[[3-(3-fluoro-4-(1,2,4-triazolyl)phenyl)-2-oxo-5-oxazolidinyl]methyl]-4-(2,4-dimethylphenyl)-4-oxobutanamide;
44) (S)-N-[[3-(3-fluoro-4-(1,2,4-triazolyl)phenyl)-2-oxo-5-oxazolidinyl]methyl]-4-oxo-4-(4-thiomethylphenyl)butanamide;
45) (S)-N-[[3-(3-fluoro-4-(1,2,4-triazolyl)phenyl)-2-oxo-5-oxazolidinyl]methyl]-4-(2',2'-dimethyl-4-ethylphenyl)-4-oxobutanamide;
46) (S)-N-[[3-(3-fluoro-4-(1,2,4-triazolyl)phenyl)-2-oxo-5-oxazolidinyl]methyl]-4-(2'-methyl-4-propylphenyl)-4-oxobutanamide;
47) (S)-N-[[3-(3-fluoro-4-(1,2,4-triazolyl)phenyl)-2-oxo-5-oxazolidinyl]methyl]-4-oxo-4-(2-thienyl)butanamide;
48) (S)-N-[[3-(3-fluoro-4-(1,2,4-triazolyl)phenyl)-2-oxo-5-oxazolidinyl]methyl]-4-(2-naphthyl)-4-oxobutanamide;
49) (S)-N-[[3-(3-fluoro-4-(1,2,4-triazolyl)phenyl)-2-oxo-5-oxazolidinyl]methyl]-4-(4-chlorophenyl)-4-oxobutanamide;
50) (S)-N-[[3-(3-fluoro-4-(1,2,4-triazolyl)phenyl)-2-oxo-5-oxazolidinyl]methyl]-4-(4-acetamidophenyl)-4-oxobutanamide;
51) (S)-N-[[3-(3-fluoro-4-(1,2,4-triazolyl)phenyl)-2-oxo-5-oxazolidinyl]methyl]-4-(2,4-difluorophenyl)-4-oxobutanamide;
52) (S)-N-[[3-(3-fluoro-4-piperidylphenyl)-2-oxo-5-oxazolidinyl]methyl]-4-oxo-4-(2-thienyl)butanamide;
53) (S)-N-[[3-(3-fluoro-4-piperidylphenyl)-2-oxo-5-oxazolidinyl]methyl]-4-(2'-methyl-4-propylphenyl)-4-oxobutanamide;
54) (S)-N-[[3-(3-fluoro-4-piperidylphenyl)-2-oxo-5-oxazolidinyl]methyl]-4-(4-acetamidophenyl)-4-oxobutanamide;
55) (S)-N-[[3-(3-fluoro-4-piperidylphenyl)-2-oxo-5-oxazolidinyl]methyl]-4-oxo-4-phenylbut-2-enamide;
56) (S)-N-[[3-(3-fluoro-4-pyrrolidinylphenyl)-2-oxo-5-oxazolidinyl]methyl]-4-oxo-4-(4-thiomethylphenyl)butanamide;
57) (S)-N-[[3-(3-fluoro-4-pyrrolidinylphenyl)-2-oxo-5-oxazolidinyl]methyl]-4-(2-naphthyl)-4-oxobutanamide;
58) (S)-N-[[3-(3-fluoro-4-pyrrolidinylphenyl)-2-oxo-5-oxazolidinyl]methyl]-4-(2'-methyl-4-propylphenyl)-4-oxobutanamide;
59) (S)-N-[[3-(3-fluoro-4-pyrrolidinylphenyl)-2-oxo-5-oxazolidinyl]methyl]-4-(2',2'-dimethyl-4-ethylphenyl)-4-oxobutanamide;
60) (S)-N-[[3-(3-fluoro-4-pyrrolidinylphenyl)-2-oxo-5-oxazolidinyl]methyl]-4-(4-acetamidophenyl)-4-oxobutanamide;
61) (S)-N-[[3-(3-fluoro-4-pyrrolidinylphenyl)-2-oxo-5-oxazolidinyl]methyl]-4-oxo-4-phenylbut-2-enamide;
62) (S)-N-[[3-(3-fluoro-4-thiomorpholinylphenyl)-2-oxo-5-oxazolidinyl]methyl]-4-(4-methoxyphenyl)-4-oxobutanamide;
63) (S)-N-[[3-(3-fluoro-4-thiomorpholinylphenyl)-2-oxo-5-oxazolidinyl]methyl]-4-(2,4-dimethylphenyl)-4-oxobutanamide;
64) (S)-N-[[3-(3-fluoro-4-thiomorpholinylphenyl)-2-oxo-5-oxazolidinyl]methyl]-4-oxo-4-(2-thienyl)butanamide;

65) (S)-N-[[3-(3-fluoro-4-thiomorpholinylphenyl)-2-oxo-5-oxazolidinyl]methyl]-4-(4-acetamidophenyl)-4-oxobutanamide;
66) (S)-N-[[3-(3-fluoro-4-piperidylphenyl)-2-oxo-5-oxazolidinyl]methyl]-4-oxo-4-(4-thiomethylphenyl)butanamide;
67) (S)-N-[[3-(3-fluoro-4-piperidylphenyl)-2-oxo-5-oxazolidinyl]methyl]-4-(2-naphthyl)-4-oxobutanamide;
68) (S)-N-[[3-(3-fluoro-4-piperidylphenyl)-2-oxo-5-oxazolidinyl]methyl]-4-(2',2'-dimethyl-4-ethylphenyl)-4-oxobutanamide;
69) (S)-N-[[3-(3-fluoro-4-benzotriazolylphenyl)-2-oxo-5-oxazolidinyl]methyl]-4-oxo-4-(4-thiomethylphenyl)butanamide;
70) (S)-N-[[3-(3-fluoro-4-benzotriazolylphenyl)-2-oxo-5-oxazolidinyl]methyl]-4-(2-naphthyl)-4-oxobutanamide;
71) (S)-N-[[3-(3-fluoro-4-benzotriazolylphenyl)-2-oxo-5-oxazolidinyl]methyl]-4-(2',2'-dimethyl-4-ethylphenyl)-4-oxobutanamide;
72) (S)-N-[[3-(3-fluoro-4-benzotriazolylphenyl)-2-oxo-5-oxazolidinyl]methyl]-4-oxo-4-phenylbut-2-enamide;
73) (S)-N-[[3-(3-fluoro-4-benzotriazolylphenyl)-2-oxo-5-oxazolidinyl]methyl]-4-(4-acetamidophenyl)-4-oxobutanamide;
74) (S)-N-[[3-(3-fluoro-4-thiomorpholinylphenyl)-2-oxo-5-oxazolidinyl]methyl]-4-(2',2'-dimethyl-4-ethylphenyl)-4-oxobutanamide;
75) (S)-N-[[3-(3-fluoro-4-thiomorpholinylphenyl)-2-oxo-5-oxazolidinyl]methyl]-4-oxo-4-phenylbut-2-enamide;
76) (S)-N-[[3-(3-fluoro-4-thiomorpholinylphenyl)-2-oxo-5-oxazolidinyl]methyl]-4-(2-naphthyl)-4-oxobutanamide;
77) (S)-N-[[3-(3-fluoro-4-thiomorpholinylphenyl)-2-oxo-5-oxazolidinyl]methyl]-4-(4-chlorophenyl)-4-oxobutanamide;
78) (S)-N-[[3-(3-fluoro-4-thiomorpholinylphenyl)-2-oxo-5-oxazolidinyl]methyl]-4-(2,4-dimethyl-4ethylphenyl)-4-oxobutanamide.

4. A compound as claimed in claim 3, wherein said compound of formula I is selected from the group of N-oxide of said compounds 1-14 and 16-78.

5. A pharmaceutical composition comprising a) at least one of I) a compound as in any one of claims 1 to 4 and II) its pharmaceutically acceptable salts and b) a pharmaceutically acceptable carrier.

6. A pharmaceutical composition as claimed in claim 5 for use as an antimycobacterial pharmaceutical composition.

7. A pharmaceutical composition according to claim 5, comprising a solid or liquid preparation.

8. A pharmaceutical composition as claimed in claim 7 for oral or parenteral administration.

9. A method of inhibiting the growth of a mycobacterial cell with at least one of a compound of formula (I)

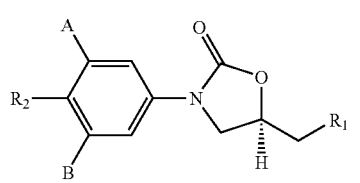

(I)

wherein,

A is either hydrogen or fluorine,

B is either hydrogen or fluorine, wherein one of A and B is hydrogen and the other is fluorine, $R_1$ is a group of formula,

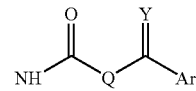

wherein,

Q is either an alkyl group of two carbon atoms, an alkene group of two carbon atoms or an alkyne group of two carbon atoms Y is oxygen;

Ar is a substituted phenyl ring or a substituted pyridine ring of formula

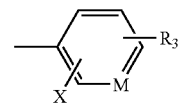

or Ar is a five membered ring of formula

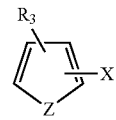

or Ar is a fused bicyclic phenyl or pyridine ring of formula

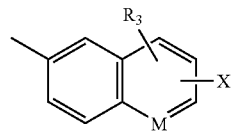

wherein,

M is either CH or N is CH, NH, O, or S,

X is a group selected from $OR_4$, $NR_4R_5$, $NO_2$, $SR_4$, $SOOR_4$, $SOONR_4R_5$, F, Cl, Br or I, wherein R4 is as defined hereinbefore, and $R_3$ is an alkyl group of 1-4 carbon atoms, both saturated and unsaturated, which can be straight or branched; cycloalkyl of 3-7 carbon atoms; CHO, —COOH, —COOR$_4$; COCR$_4$; CN; aryl or heteroaryl;

wherein, $R_4$ is an alkyl group of 1-4 carbon atoms, an alkene of 3-6 carbon atoms, an alkyne of 3-6 carbon atoms;

$R_5$ is hydrogen or $R_4$ $R_2$ is selected from the groups shown below, and the corresponding N-oxides thereof;

Heteroaryl or Heterocycloalkyl wherein K is O, S, SO, SO$_2$, or CH$_2$; and its pharmaceutically acceptable salt with or without any pharmaceutically acceptable carrier thereof.

10. The method according to claim 9, wherein the mycobacterial cell inhibited is any one or more of *Mycobacterium tuberculosis*, drug resistant *Mycobacterium tuberculosis, M. avium*-intracellular complex, *M. fortuitum* and *M. kansai*.

11. A method of treating mycobacterial conditions in a mammal which comprises administration of an antimycobacterially effective amount of at least one of a compound of formula (I)

(I)

wherein,

A is either hydrogen or fluorine,

B is either hydrogen or fluorine, wherein one of A and B is hydrogen and the other is fluorine, R$_1$ is a group of formula, wherein, Q is either an alkyl group of two carbon atoms, an alkene group of two carbon atoms or an alkyne group of two carbon atoms Y is oxygen;

Ar is a substituted phenyl ring or a substituted pyridine ring of formula or Ar is a five membered ring of formula or Ar is a fused bicyclic phenyl or pyridine ring of formula wherein, M is either CH or N Z is CH, NH, O, or S, X is a group selected from OR$_4$, NR$_4$R$_5$, NO$_2$, SR$_4$, SOOR$_4$, SOONR$_4$R$_5$, F, Cl, Br or I, wherein R$_4$ is as defined hereinbefore, and R$_3$ is an alkyl group of 1-4 carbon atoms, both saturated and unsaturated, which can be straight or branched; cycloalkyl of 3-7 carbon atoms; CHO, —COOH, —COOR$_4$; COCR$_4$; CN; aryl or heteroaryl;

wherein,

R$_4$ is an alkyl group of 1-4 carbon atoms, an alkene of 3-6 carbon atoms, an alkyne of 3-6 carbon atoms;

R$_5$ is hydrogen or R$_4$

R$_2$ is selected from the groups shown below, and the corresponding N-oxides thereof;

Heteroaryl or Heterocycloalkyl wherein K is O, S, SO, SO$_2$, or CH$_2$; and its pharmaceutically acceptable salt with or without any pharmaceutically acceptable carrier thereof.

12. A method as claimed in claim 11 wherein the condition treated is tuberculosis in mammals.

13. A method of treatment as claimed in any one of claims 9 to 12 wherein the mode of administration is oral or parenteral.

14. A method of preparation of the compound of formula I of claim 1 and/or its pharmaceutically acceptable salts comprising:

coupling of the amino fragment of compound of formula II

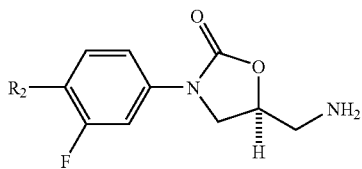

with a carboxylic acid of formula III,

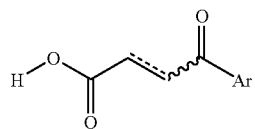

wherein R2 has the same meaning as given in claim 1.

15. A method as claimed in claim 14 wherein the compound of formula II is preferably selected from (S)-N-[3-(3-fluoro-4-morpholinylphenyl)-2-oxo-5-oxazoidinyl]methyl amine, (S)-N-[3-(3-fluoro-4-thiomorpholinylphenyl)-2-oxo-5-oxazolidinyl]methyl amine, (S)-N-[3-(3-fluoro-4-piperidylphenyl)-2-oxo-5-oxazolidinyl]methyl amine,(S)-N-[3-(3-fluoro-4-benzylpiperazinylphenyl)-2-oxo-5-oxazolidinyl]methyl amine, (S)-N-[3-(3-fluoro-4-pyrrolidinylphenyl)-2-oxo-5-oxazolidinyl]methyl amine, (S)-N-[3-(3-fluoro-4-(1,2,4-triazolyl)phenyl)-2-oxo-5-oxazolidinyl]methyl amine, (S)-N-[3-(3-fluoro-4-benzotriazolylphenyl)-2-oxo-5-oxazolidinyl]methyl amine, and (S)-N-[3-(3-fluoro-4-[methylbenzylamino]phenyl)-2-oxo-5-oxazolidinyl]methyl amine.

16. A method as claimed in any one of claims 14 and 15 wherein the compound of formula III is selected from 4-(2-Naphthyl)-4-oxobutanoic acid, 4-Oxo-4-(2-Thienyl)butanoic acid, 4-Oxo-4-(4-thiomethyl)phenylbutanoic acid, 4-oxo-4-(2'methylpropyl)phenylbutanoic acid, 4-Oxo-4-(2',2'dimethylethyl)phenylbutanoic acid, 4-(4-methylphenyl)-4-oxobutanoic acid, 4-(2,4-dimethylphenyl)-4-oxobutanoic acid, 4-(4-methoxyphenyl)-4-oxobutanoic acid, 4-(4-chlorophenyl)-4-oxobutanoic acid, 4-(2,4-dichlorophenyl)-4-oxobutanoic acid, 4-(2,4-difluorophenyl)-4-oxobutanoic acid, 4-(2-Naphthyl)-4-oxobutanoic acid, 4-(4-acetamidophenyl)-4-oxobutanoic acid, (2E/Z)-Oxo-4-phenylbut-2-enoic acid, and 4-oxo-4-phenyl-but-2-ynoic acid.

\* \* \* \* \*